US011266311B2

(12) United States Patent
Tyler

(10) Patent No.: US 11,266,311 B2
(45) Date of Patent: Mar. 8, 2022

(54) SYSTEMS AND METHODS FOR GENERATING AN ELASTOGRAM OF BRAIN TISSUE USING MESOSCOPIC WAVELENGTH ULTRASOUND

(71) Applicant: William Tyler, Newton, MA (US)

(72) Inventor: William Tyler, Newton, MA (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 75 days.

(21) Appl. No.: 16/618,101

(22) PCT Filed: Jun. 8, 2018

(86) PCT No.: PCT/US2018/036660
§ 371 (c)(1),
(2) Date: Nov. 27, 2019

(87) PCT Pub. No.: WO2018/227088
PCT Pub. Date: Dec. 13, 2018

(65) Prior Publication Data
US 2020/0107725 A1 Apr. 9, 2020

Related U.S. Application Data

(60) Provisional application No. 62/516,834, filed on Jun. 8, 2017.

(51) Int. Cl.
*A61B 5/055* (2006.01)
*A61B 8/08* (2006.01)
(Continued)

(52) U.S. Cl.
CPC .......... *A61B 5/0042* (2013.01); *A61B 5/0035* (2013.01); *A61B 5/055* (2013.01);
(Continued)

(58) Field of Classification Search
CPC combination set(s) only.
See application file for complete search history.

(56) References Cited

U.S. PATENT DOCUMENTS 5,316,000 A * 5/1994 Chapelon ......... A61B 17/22004
310/334
5,952,828 A 9/1999 Rossman et al.
(Continued)

FOREIGN PATENT DOCUMENTS

WO 2009081339 A1 7/2009
WO 2010009141 A1 1/2010
(Continued)

OTHER PUBLICATIONS

Lindsey, Brooks D et al. "The ultrasound brain helmet: new transducers and volume registration for in vivo simultaneous multi-transducer 3-D transcranial imaging." IEEE transactions on ultrasonics, ferroelectrics, and frequency control vol. 58,6 (2011): 1189-202. doi: 10.1109/TUFFC.2011.1929 (Year: 2011).*
(Continued)

*Primary Examiner* — Boniface Ngathi
(74) *Attorney, Agent, or Firm* — Withrow & Terranova, P.L.L.C.

(57) ABSTRACT

Methods, systems, and devices for mechanically disturbing tissues of the central nervous system including a brain of a subject are provided. An elastogram of brain tissue may be generated using mesoscopic wavelength ultrasound composed of longitudinal waves in brain tissues to produce micromechanical disturbances of brain nuclei and circuits for characterization of their mechanical properties (e.g., stiffness, elasticity, rigidity, viscoelasticity). A magnetic resonance elastography (MRE) system includes an MRE engine in electronic communication with at least one transducer and with a magnetic resonance imaging (MRI) device. The MRE engine is configured to electronically control
(Continued)

operation of the at least one transducer to emit ultrasound, to electronically receive, from the MRI device, at least one signal indicative of measurements of displacement of the brain tissue by the ultrasound, and to electronically generate an elastogram of the brain tissue based on the at least one signal.

18 Claims, 23 Drawing Sheets

(51) Int. Cl.
    *A61B 5/00*         (2006.01)
    *G01R 33/48*      (2006.01)
    *G01R 33/563*     (2006.01)

(52) U.S. Cl.
    CPC ............ *A61B 8/0808* (2013.01); *A61B 8/485* (2013.01); *A61B 8/5261* (2013.01); *G01R 33/4814* (2013.01); *G01R 33/56358* (2013.01)

(56) References Cited

U.S. PATENT DOCUMENTS

| | | | |
|---|---|---|---|
| 6,037,774 | A | 3/2000 | Felmlee et al. |
| 6,862,468 | B2 | 3/2005 | Smith |
| 7,034,535 | B2 | 4/2006 | Ehman et al. |
| 7,331,926 | B2 | 2/2008 | Varghese et al. |
| 7,674,229 | B2 | 3/2010 | Hynynen et al. |
| 7,896,821 | B1* | 3/2011 | Magnin .............. A61H 23/0245 601/2 |
| 8,591,419 | B2* | 11/2013 | Tyler .................... C12N 5/0619 600/439 |
| 8,858,440 | B2 | 10/2014 | Tyler |
| 9,403,038 | B2 | 8/2016 | Tyler |
| 10,556,132 | B2 | 2/2020 | Tyler |
| 2003/0220556 | A1* | 11/2003 | Porat .................... A61B 5/0051 600/407 |
| 2004/0122323 | A1* | 6/2004 | Vortman .................. A61N 7/02 600/459 |
| 2004/0215075 | A1 | 10/2004 | Zagzebski et al. |
| 2006/0241529 | A1* | 10/2006 | Hynynen ............. A61B 8/0816 601/2 |
| 2007/0161891 | A1* | 7/2007 | Moore ............. G01R 33/56358 600/421 |
| 2009/0221916 | A1 | 9/2009 | Konofagou et al. |
| 2010/0049029 | A1* | 2/2010 | Li .......................... A61B 5/055 600/410 |
| 2010/0125193 | A1* | 5/2010 | Zadicario ................ A61N 7/02 600/411 |
| 2011/0025333 | A1* | 2/2011 | Ehman ............. G01R 33/56358 324/318 |
| 2011/0137166 | A1 | 6/2011 | Klee et al. |
| 2011/0178441 | A1* | 7/2011 | Tyler .................... A61B 5/0476 601/2 |
| 2012/2669415 | | 10/2012 | Glaser et al. |
| 2012/0289869 | A1* | 11/2012 | Tyler .................. A61B 5/04008 601/2 |
| 2013/0131490 | A1* | 5/2013 | Huston, III ...... G01R 33/56358 600/410 |
| 2013/0144192 | A1* | 6/2013 | Mischelevich .......... A61N 7/00 601/2 |
| 2013/0237820 | A1* | 9/2013 | Vappou ................ A61B 8/0858 600/438 |
| 2015/0148675 | A1* | 5/2015 | Haupt .................. A61B 8/5215 600/438 |
| 2016/0220850 | A1 | 8/2016 | Tyler |
| 2016/0243381 | A1* | 8/2016 | Alford ..................... A61N 7/00 |
| 2016/0374586 | A1* | 12/2016 | Johnson ............... A61B 5/4244 600/410 |
| 2018/0177491 | A1* | 6/2018 | Hynynen ............. A61B 8/4494 |
| 2019/0105517 | A1 | 4/2019 | Tyler |
| 2019/0160309 | A1* | 5/2019 | Ebbini ................. A61B 8/4488 |

FOREIGN PATENT DOCUMENTS

| | | |
|---|---|---|
| WO | 2011057028 A1 | 5/2011 |
| WO | 2016185192 A1 | 11/2016 |
| WO | 2019046757 A1 | 3/2019 |

OTHER PUBLICATIONS

Notification of Transmittal (Form PCT/ISA/220), International Search Report (Form PCT/ISA/210), and Written Opinion of the International Searching Authority (Form PCT/ISA/237) for International Application No. PCT/US2018/036660 dated Sep. 7, 2018 (11 pages).

Pek-Ugay et al., "Tabletop magnetic resonance elastography for the measurement of viscoelastic parameters of small tissue samples," Journal of Magnetic Resonance 251, pp. 13-18 (Dec. 2014).

Green et al., "High Resolution 3D Brain MR-Elastography," Proc. IntL Soc. Mag. Reson. Med. 14, p. 2021 (2006).

Sack et al., "The Influence of Physiological Aging and Atrophy on Brain Viscoelastic Properties in Humans," PLoS ONE6(9): e23451. doi: 10.1371/journal.pone.0023451 (Sep. 2011).

Sack et al. "The impact of aging and gender on brain viscoelasticity," NeuroImage 46, pp. 652-657, Elsevier Inc. (2009).

Hamhaber et al., "In Vivo Magnetic Resonance Elastography of Human Brain at 7 T and 1 5 T," Journal of Magnetic Resonance Imaging 32, pp. 577-583, Wiley-Liss, Inc. (2010).

Green et al., "In vivo brain viscoelastic properties measured by magnetic resonance elastography," NMR Biomed 21, pp. 755-764, John Wiley & Sons, Ltd. (2008).

Zhang et al., "Viscoelastic properties of human cerebellum using magnetic resonance elastography," Journal of Biomechanics 44, pp. 1909-1913, Elsevier Ltd. (2011).

Latta, et al., "A convertible pneumatic actuator for brain and phantom elastography," Proc. Inti. Soc. Mag. Reson. Med. 18, p. 1054(2010).

Chen et al., "Optimization of Encoding Gradients for MR-ARFI," Magnetic Resonance in Medicine 63, pp. 1050-1058, Wiley-Liss, Inc. (2010).

Clayton et al., "Quantitative Measurement of Brain Deformation Caused by Pressure Loading of the Skull," Proc. Intl. Soc. Mag. Reson. Med. 19, p. 3488 (2011).

Sack et al., "Non-invasive measurement of brain viscoelasticity using magnetic resonance elastography," NMR Biomed. 21, pp. 265-271, John Wiley & Sons, Ltd. (2008).

Clayton et al., "Brain Response to Extracranial Pressure Excitation Imaged in vivo by MR Elastography," Mechanics of Biological Systems and Materials, vol. 2, Conference Proceedings of the Society for Experimental Mechanics Series 9999, DOI 10.1007/ 978-1-4614-0219-0_7, The Society for Experimental Mechanics, Inc. (2011).

Mariappan, et al., "Magnetic Resonance Elastography: A Review," Clinical Anatomy 23, pp. 497-511, Wiley-Liss, Inc. (2010).

Klatt et al., "Noninvasive assessment of the rheological behavior of human organs using multifrequency MR elastography: a study of brain and liver viscoelasticity," Phys. Med. Biol. 52, pp. 7281-7294, IOP Publishing (2007).

Glaser et al., "Review of MR Elastography Applications and Recent Developments," Journal of Magnetic Resonance Imaging 36, pp. 757-774, Wiley Periodicals, Inc. (2012).

Kruse et al., "Magnetic resonance elastography of the brain," NeuroImage 39, pp. 231-237, Elsevier Inc. (2008).

Mace et al., "In Vivo Mapping of Brain Elasticity in Small Animals Using Shear Wave Imaging," IEEE Transactions on Medical Imaging, vol. 30, No. 3, pp. 550-558, IEEE (Mar. 2011).

Souchon et al., "Transient MR Elastography (t-MRE) Using Ultrasound Radiation Force: Theory, Safety, and Initial Experiments In Vitro," Magnetic Resonance in Medicine 60, pp. 871-881, Wiley-Liss, Inc. (2008).

U.S. Appl. No. 16/642,750, Hool et al., filed Feb. 27, 2020.
U.S. Appl. No. 16/779,442, Tyler, filed Jan. 31, 2020.

(56) References Cited

OTHER PUBLICATIONS

Boulet, T. et al., "Microscopic magnetic resonance elastography of traumatic brain injury model," Journal of Neuroscience Methods, vol. 201, 2011, Elsevier B.V., pp. 296-306.

McCracken, P.J. et al., "Mechanical transient-based magnetic resonance elastography," Magnetic Resonance in Medicine, vol. 53, 2005, Wiley-Liss, Inc., pp. 628-639.

Murphy, M.C., et al., "Decreased brain stiffness in alzheimer's disease determined by magnetic resonance alastography," Journal of Magnetic Resonance Imaging, vol. 34, 2011, Wiley-Liss, Inc., pp. 494-498.

Palmeri, M.L. et al., "Acoustic radiation force-based elasticity imaging methods," Interface Focus, vol. 1, Issue 4, 2011, The Royal Society, pp. 553-564.

Zheng, Y. et al., "Magnetic resonance elastography with twin pneumatic drivers for wave compensation," Proceedings of the 29th Annual International Conference of the IEEE EMBS, Aug. 23-26, 2007, Lyon, France, IEEE, pp. 2611-2613.

International Preliminary Report on Patentability for International Patent Application No. PCT/US2018/036660, dated Dec. 19, 2019, 10 pages.

\* cited by examiner $f = 0.25$ MHz, T = 4 μsec
$\lambda = 6.16$ mm in brain $f = 1.0$ MHz, T = 1 μsec
$\lambda = 1.54$ mm in brain $f = 2.0$ MHz, T = 0.5 μsec
$\lambda = 0.77$ mm in brain $f = 1.5$ MHz, T = 0.67 μsec
$\lambda = 1.03$ mm in brain

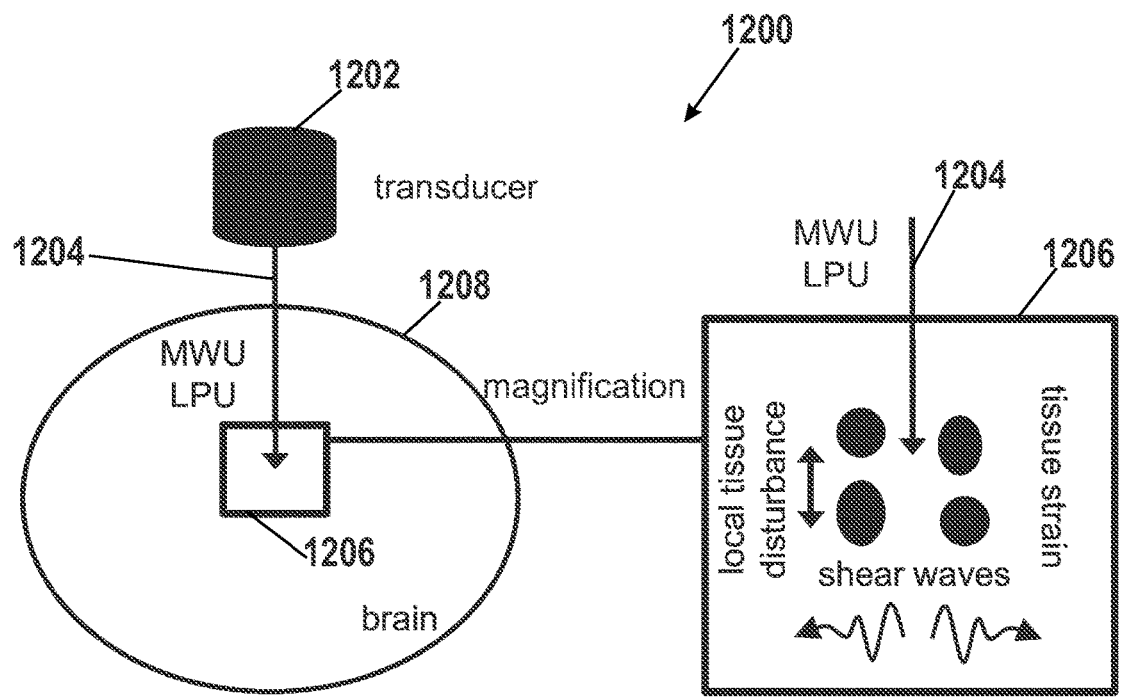
FIG. 12
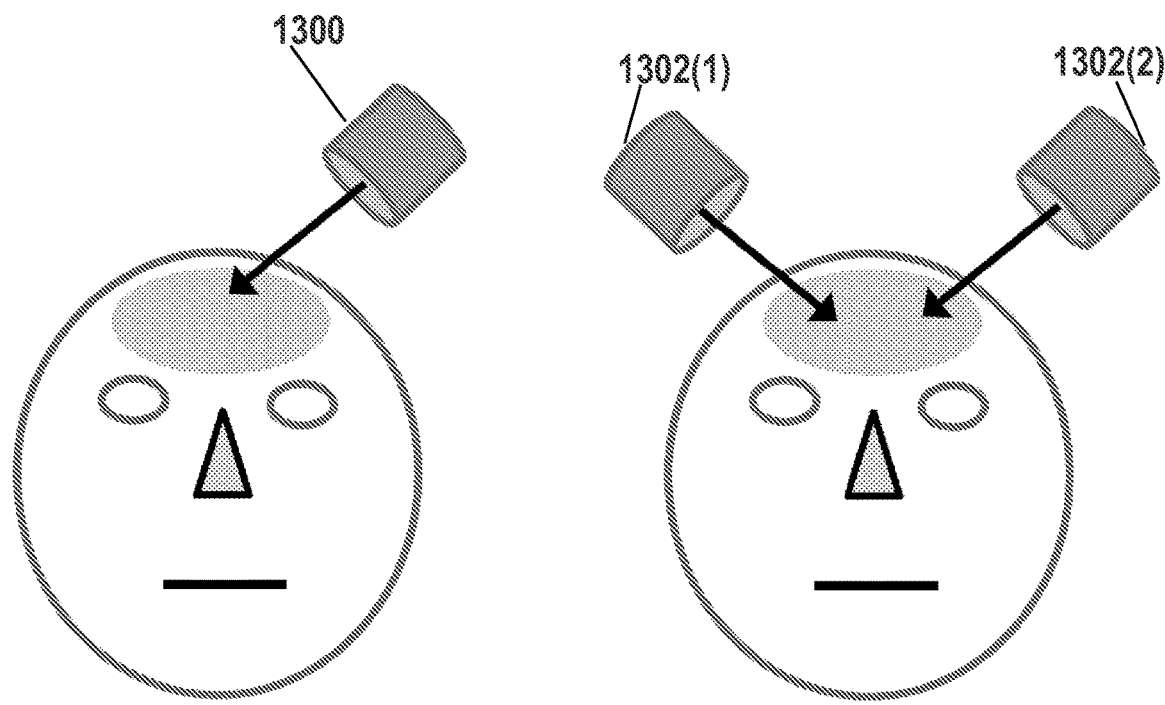
FIG. 13A
FIG. 13B

SYSTEMS AND METHODS FOR GENERATING AN ELASTOGRAM OF BRAIN TISSUE USING MESOSCOPIC WAVELENGTH ULTRASOUND

STATEMENT OF RELATED APPLICATION(S)

This application is the U.S. national phase under 35 U.S.C. § 371 of International Application No. PCT/US2018/036660 filed Jun. 8, 2018, and further claims priority to U.S. Provisional Patent Application No. 62/516,834 filed Jun. 8, 2017 wherein the entire contents of the foregoing applications are hereby incorporated by reference herein.

TECHNICAL FIELD

This disclosure relates to delivery of mechanical waves in the form of ultrasound to the central nervous system of a subject for the purpose of generating mesoscopic mechanical disturbances in tissues and cells to characterize and interrogate the mechanical properties (e.g., rigidity, stiffness, elasticity, viscoelasticity, etc.) of neural circuits and tissues. In particular, the disclosure related to systems and methods for generating an elastogram of brain tissue using mesoscopic wavelength ultrasound.

BACKGROUND

Data from studies characterizing the macroscopic physical characteristics of the brain indicates that the brain is a viscoelastic material and is one of the softest tissues in the body. Many values describing the elastic properties of the brain have been estimated by converting the shear modulus (G) of brain to the elastic modulus (E) where the brain is assumed to have Poisson's ratio (v)=0.5 and E=2G(1+v). In particular, the elastic modulus (E) of an isotropic solid is defined as a constant describing a stress/strain ratio. Rodent and human brains have been described as having an estimated E ranging from 0.1 to 16 kPa (1 $nN/\mu m^2$=1000 Pa). The ratio of transverse strain to axial strain in the direction of the stretching force defines the Poisson's ratio (v) of a material.

Moduli that are generally useful for describing the elasticity of a solid include the elastic modulus (E), the shear modulus (G), the bulk modulus (K), and the complex modulus. The elastic modulus (i.e., longitudinal elasticity) of a solid, also known as the Young's modulus (E) is defined as E=stress/strain. The shear modulus (G) of a material can be described by G=E/(2(1+v)), where v is Poisson's ratio. The bulk modulus (K) of a material can be described as K=E/(3(1−2v)). The complex modulus (i.e., dynamic modulus) is the ratio of stress to strain under vibratory conditions.

The elastic modulus, shear modulus, bulk modulus, and/or complex modulus can be used for describing the mechanical properties of the brain in terms of rigidity, stiffness, elasticity, viscoelasticity, etc. These properties can be estimated by using inversion and imaging approaches useful for characterizing motion, the displacement of tissues by longitudinal waves, and the propagation speed or wavelength of shear waves introduced to the body by mechanical waves. For example, elastography uses magnetic resonance (MR) or ultrasound imaging to estimate the stiffness of tissues by imaging their responses to sound (shear) waves propagated through the body.

FIG. 1 is a diagram illustrating properties of a mechanical wave in both spatial and time scales. In particular, the mechanical wave 100 includes a velocity 102, a pulse duration 104, a pulse length 106, a period 108, and a wavelength 110.

FIG. 2 is a diagram illustrating longitudinal waves 200 (i.e., primary wave, P wave, compressional wave, etc.) and shear waves 202 (i.e., secondary wave, S wave). With a longitudinal wave 200, particles in a medium 204 move in the same direction that the longitudinal wave 200 is moving (i.e., direction of wave propagation 206). In this manner, the longitudinal wave 200 travels through the medium 204 by means of compression 208 and dilation 210. Comparatively, shear waves 202 move slower than longitudinal waves 200. Shear waves 202 move particles of the medium 204 in a direction generally perpendicular to the direction of wave propagation 206, thereby providing a wavelength and amplitude for the medium 204.

Referring to FIGS. 3A-4D, magnetic resonance elastography (MRE) is useful for characterizing and mapping the nonlinear viscoelastic properties of the intact human brain. Stiffness of brain regions significantly vary in normal humans and these mechanical properties change across age and disease states. MRE is conducted by generating a strain elastogram from MR-imaging data of tissue responses to externally applied quasi-static compression or harmonic shear waves. FIGS. 3A-3C graphically illustrate phantom tissue displacements driven by mechanical waves having a frequency of 100 Hz. In particular, FIG. 3A is an amplitude diagram 300 illustrating amplitude of phantom tissue as a mechanical wave propagates through the phantom tissue. Concentric rings of low amplitude 302 and high amplitude 304 sections of the mechanical wave are formed as the mechanical wave moves through the phantom tissue. FIG. 3B is a diagram 306 illustrating an echo planar image, which does not include any contrast without applying mathematical processes to the image. FIG. 3C is a diagram 308 illustrating shear stiffness of the phantom tissue as the mechanical wave propagates through the phantom tissue. As shown, there are generally concentric sections of low shear stiffness 310, medium shear stiffness 312, and high shear stiffness 314.

FIGS. 4A-4D graphically illustrate brain tissue displacements driven by mechanical waves having a frequency of 100 Hz. In particular, FIG. 4A is an echo planar image 400. FIG. 4B is an amplitude diagram 402 illustrating amplitude of brain tissue as a mechanical wave propagates through the brain tissue. As shown, there are areas of low amplitude 404 and areas of high amplitude 406. FIGS. 4C and 4D are elastograms 408 illustrating shear stiffness of the brain tissue as the mechanical wave propagates through the brain tissue. As shown, there are areas of low shear stiffness 410, medium shear stiffness 412, and high shear stiffness 414.

Elastograms may be used in clinical diagnostics, since many diseases are associated with changes in cellular elasticity. MRE has been used to map and characterize the viscoelastic properties of normal, aged, and diseased human brains. MRE has also been shown to be useful in characterizing traumatic brain injury (TBI) in rodent models. An increase in the number and breadth of observations from neuroimaging studies employing MRE indicates a strong and growing interest in determining how the mechanical properties of a brain relate to its function and dysfunction. However, there is a need to improve the spatial resolution of current elastographic imaging methods including MRE.

Current methods of elastographic imaging do not implement mechanical waves adequately matched to functional brain nuclei or circuits. For example, many commonly applied systems and methods for introducing mechanical waves to brain tissue rely on passive drivers remotely actuated by pressure displacements driven by an acoustic speaker, active transducer, or other piezoelectric element to mechanically displace the head of a subject. For example, FIG. 5A illustrates a head actuator 500 configured to move the entire head 502 of a subject. Similarly, FIG. 5B also illustrates an actuator 504 configured to move the entire head 502 of a subject when the head 502 of the subject is placed on the actuator 504, with the actuator being arranged proximate to a MRI head coil 503. As an alternative, FIG. 5B illustrates an actuator 506 configured to be received in the mouth and clenched by jaws 508 of a subject to move the entire head 502 of the subject by being clenched in the jaws 508. These coarse mechanical approaches can cause poor spatial resolution conferred by the longitudinal wavelengths used to displace the body or head and subsequently generate shear waves in the body's tissues or brain. In other words, the brain tissue displacement is generalized, not localized.

Some ultrasound imaging-based approaches to elastography not only use ultrasound for imaging, but also rely on ultrasound to displace tissue. Acoustic radiation force imaging (ARFI), shear wave elasticity imaging (SWEI), and supersonic shear imaging or shear wave imaging (SWI) methods often rely on ultrasound-mediated tissue displacements produced by ultrasound having an acoustic frequency typically greater than 2 MHz, or similar to that used in ultrasound diagnostic imaging. Transient magnetic resonance elastography (tMRE) also relies on temporally specific ultrasound waveforms typically using an acoustic frequency >2 MHz to displace soft tissues, such as the liver, for mechanical characterization. These approaches, however, provide short longitudinal wavelengths having microscopic, longitudinal spatial length scales approximately 0.77 millimeters or shorter in brain at an acoustic frequency (f) of about 2 MHz or greater.

On the other hand, mechanical displacement of the head and the brain for conventional magnetic resonance elastography (MRE) typically uses audible acoustic frequencies ranging from about 50 Hz to about 2000 Hz. These approaches confer longitudinal mechanical waves having macroscopic spatial lengths ranging from approximately 0.77 meters or 770 millimeters for 2000 Hz to 30.8 meters for 50 Hz in the brain.

The conversion of longitudinal pressure waves to shear waves in different tissues is complex and dependent on many factors including the shear modulus (G), the elastic modulus (E), the complex modulus, the geometry and mechanical properties of the surrounding cellular environment, and temperature of the tissue, etc. Differences in tissue mechanical properties at boundary sites, such as the skull and cerebrospinal fluid interface, the cerebrospinal fluid and grey matter interface, or grey matter and white matter interfaces further complicate wave mode conversions in tissues. Irrespective of these complexities however, targeting distinct brain circuits with mechanical waves having either short (microscopic) or long (macroscopic) longitudinal spatial quantities is difficult, and mechanical properties derived therefrom are prone to instability and error. Accordingly, there is a need for improved methods and systems for providing displacement of brain tissues using mechanical waves.

Cells in the brain including glial cells, neurons, stem cells, neural progenitors, and cells comprising vasculature have variable diameters ranging from about 5 to 40 micrometers. Neurons and other cells in the brain can possess neuronal processes extending from tens of microns to several millimeters. Groups of cells approximately tens to tens of thousands or hundreds of thousands in number communicate with one another to form functional brain circuits or nuclei. These circuits form spatially discrete brain nuclei having mesoscopic spatial length scales of about 1 to 20 millimeters and are devoted to regulating various aspects of executive function, motor function, visual function, auditory function, somatosensory function, physiological arousal, and conscious binding of experience.

Referring to FIGS. 6A-6D, spatially discrete brain circuits having mesoscopic or millimeter length scales can serve unique functions. FIG. 6A is a side view of a brain 600. FIG. 6B is a cross-sectional top view of the brain of FIG. 6A taken along section line 601 in FIG. 6A. The brain 600 includes the lateral ventricle, frontal horn 602, the fornix, column 604, the frontal operculum 606, the internal capsule, genu 608, the Thalamus, VA 610, the internal capsule, posterior limb 612, the velum interpositum and internal cerebral vein 614, the calcarine fissure 616, the corpus callosum, splenium 618, the lateral ventricle, trigone 620, the thalamus, pul 622, the thalamus, LP 624, the parietal operculum 626, the putamen 628, the interventricular foramen 630, the internal capsule, anterior limb 632, the caudate nucleus, head 634. FIG. 6C is a top view illustrating thalamic nuclei and connections. The brain includes the anterior 636, ventral anterior 638, reticular 640, lateral dorsal 642, ventral lateral 644, interlaminar 646, ventral posterior 648, lateral posterior 650, mediodorsal 652, pulvinar 654, lateral geniculate 656, medial geniculate 658. The ventral anterior 636 communicates to the prefrontal cortex 660 and from the globus pallidus 662. The ventral lateral 644 communicates to the supplementary motor area 664, from the globus pallidus 666, to the motor cortex 668, and from the cerebellum 670. The ventral posterior 648 communicates to the somatic sensory cortex 672 from medial, spinal, and trigeminal lemnisci 674. The lateral geniculate 656 communicates from the optic track 676 and to the primary visual cortex 678. The medial geniculate 658 communicates to the primary auditory cortex 680 and from the inferior brachium 682.

Due to differences in the sizes, shapes, and physical, biochemical or molecular composition of cells comprising different functional nuclei in the brain, it should be expected that brain circuits serving different functional roles will have different mechanical properties, such as stiffness, rigidity, elasticity, and viscoelasticity. For example, as shown in FIG. 6D, the ventral lateral and ventral posterior nuclei of the thalamus are located approximately 1 millimeter adjacent to one another and serve different roles in somatosensory and motor processing. It is possible the ventral lateral and ventral posterior regions of the thalamus possess distinct mechanical properties, which may differ from one another. Current systems and methods cannot reliably determine this however, due in part to the use of inappropriately scaled longitudinal wavelengths for mechanically displacing tissues to characterize that tissue's mechanical properties. Restated, current systems and methods do not have a longitudinal wavelength resolution appropriate for targeting discrete functional brain circuits or nuclei.

FIGS. 7A-7B are elevation views of the medial surface 700 and the lateral surface 702 of the brain, respectively, including brain regions 1-47. Other functionally discrete brain circuits recognized wholly or in part by standard nomenclature, for example, Broadmann's areas, have length scales on the order of millimeters to tens of millimeters, which is similar to the thalamus and its nuclei (see FIG. 4). Thus, without appropriately scaled longitudinal waves used for displacing tissues, it would be difficult to understand how distinct mechanical tissue properties vary across functional brain circuits. In addition, using current methods known in the art, it would be difficult to adequately or reliably characterize diseased or injury-mediated changes in the mechanical properties of cells belonging to a particular brain nucleus or circuit. What is needed is a solution for mechanically disturbing targeted brain circuits for the purposes of characterizing the mechanobiological properties of the tissue composing the targeted brain circuit or brain circuits.

SUMMARY

Disclosed are systems, methods, and devices to actuate displacement of tissues by disturbing them on mesoscopic length scales using ultrasound. In particular, disclosed is a system and method for generating an elastogram of brain tissue using mesoscopic wavelength ultrasound. Systems and methods provided herein induce physical motion or displacement of tissues, evaluation of their mechanical properties with increased resolution of the tissue being evaluated. Such systems and methods provide noninvasive, mesoscopic length scale mechanical disturbance of brain tissue in a spatially and temporally precise manner using ultrasound or Mesoscopic Wavelength Ultrasound. In some embodiments, mesoscopic tissue disturbances induced by Long-period Ultrasound are used for the evaluation of brain mechanical properties using elastographic approaches, such as magnetic resonance elastography (MRE), shear wave elasticity imaging (SWEI), vibroacoustography, etc.

In an exemplary aspect, the present disclosure relates to a magnetic resonance elastography (MRE) system for generating an elastogram of at least a portion of a brain of a subject. The MRE system includes a computing device in electronic communication with at least one transducer and with a magnetic resonance imaging (MRI) device. The computing device includes at least one processor and a memory coupled to the at least one processor. The MRE system further includes an MRE engine electronically stored in the memory of the computing device and executable by the at least one processor. The MRE engine is configured to electronically control operation of the at least one transducer to emit ultrasound at a frequency from 0.1 MHz to 1 MHz and with a longitudinal wavelength from 1.54 to 15.4 millimeters to locally displace brain tissue of the subject. The MRE engine is further configured to electronically receive, from the MRI device, at least one signal indicative of measurements of displacement of the brain tissue by the ultrasound. The MRE engine is further configured to electronically generate an elastogram of the brain tissue based on the at least one signal.

In certain embodiments, the MRE system includes a single-element ultrasonic transducer. In certain embodiments, the MRE system includes a plurality of ultrasonic transducers. In certain embodiments, the plurality of transducers are configured to concentrate strain resolution at a specific target within the brain tissue.

In certain embodiments, the ultrasound includes focused ultrasound. In certain embodiments, the ultrasound includes planar ultrasound. In certain embodiments, the ultrasound has a cycle time period from 0.5 to 10 milliseconds in brain tissue. In certain embodiments, the at least one transducer is configured to emit the ultrasound for at least one burst having a duration of less than about 500 milliseconds.

In certain embodiments, the MRE engine is further configured to control operation of the at least one transducer to coordinate emission of ultrasound with one or more biological cycles of the subject. In certain embodiments, the MRE engine is further configured to derive at least one of shear moduli, elastic moduli, or bulk moduli of a brain circuit of the brain tissue.

In another exemplary aspect, the present disclosure relates to a method for generating an elastogram of at least a portion of a brain of a subject. The method includes electronically controlling, by an MRE engine executed by at least one processor of a computing device, operation of at least one transducer to emit ultrasound at a frequency from 0.1 MHz to 1 MHz and with a longitudinal wavelength from 1.54 to 15.4 millimeters to mechanically displace brain tissue of the subject, the MRE engine electronically stored in memory associated with the computing device and being coupled to the at least one processor. The method further includes electronically receiving, at the MRE engine from a magnetic resonance imaging (MRI) device, at least one signal indicative of measurements of mechanical displacement of the brain tissue by the ultrasound. The method further includes electronically generating, by the MRE engine, an elastogram of the brain tissue based on the at least one signal.

In certain embodiments, the at least one transducer includes a single-element ultrasonic transducer. In certain embodiments, the at least one transducer comprises a plurality of ultrasonic transducers. In certain embodiments, the plurality of transducers are configured to concentrate strain resolution at a specific target within the brain tissue.

In certain embodiments, the ultrasound includes focused ultrasound. In certain embodiments, the ultrasound includes planar ultrasound. In certain embodiments, the ultrasound has a cycle time period from 0.5 to 10 milliseconds in brain tissue.

In certain embodiments, the method further includes emitting, from the at least one transducer, the ultrasound for at least one burst having a duration of less than about 500 milliseconds. In certain embodiments, the method further includes controlling, by the MRE engine, operation of the at least one transducer to coordinate emission of ultrasound with one or more biological cycles of the subject. In certain embodiments, the method further includes deriving, by the MRE engine, at least one of shear moduli, elastic moduli, or bulk moduli of a brain circuit of the brain tissue.

In another exemplary aspect, the present disclosure relates to a non-transitory computer readable medium comprising program instructions for generating an elastogram of at least a portion of a brain of a subject. The program instructions are configured for electronically controlling, by an MRE engine executed by at least one processor of a computing device, operation of the at least one transducer to emit ultrasound at a frequency from 0.1 MHz to 1 MHz and with a longitudinal wavelength from 1.54 to 15.4 millimeters to mechanically displace brain tissue of a subject, the MRE engine electronically stored in memory of a computing device coupled to the at least one processor. The program instructions are further configured for electronically receiving, at the MRE engine from an MRI device, measurements of mechanical displacement of the brain tissue by the ultrasound. The program instructions are further configured for electronically generating, by the MRE engine, an elastogram of the brain tissue based on the measurements.

In certain embodiments, the program instructions are further configured for emitting, from the at least one transducer, the ultrasound for at least one burst having a duration of less than about 500 milliseconds. In certain embodiments, the program instructions are further configured for controlling, by the MRE engine, operation of the at least one transducer to coordinate emission of ultrasound with one or more biological cycles of the subject. In certain embodiments, the program instructions are further configured for deriving, by the MRE engine, at least one of shear moduli, elastic moduli, or bulk moduli of a brain circuit of the brain tissue.

Other aspects and embodiments will be apparent from the detailed description and accompanying drawings.

Those skilled in the art will appreciate the scope of the present disclosure and realize additional aspects thereof after reading the following detailed description of the certain exemplary embodiments in association with the accompanying drawings.

BRIEF DESCRIPTION OF DRAWINGS

FIG. 12 is a schematic diagram illustrating an MRE system for applying mesoscopic wavelength and long-period ultrasound for brain tissue disturbance;

FIG. 13A is a schematic diagram illustrating an MRE system with a single ultrasonic transducer;

FIG. 13B is a schematic diagram illustrating an MRE system with multiple ultrasonic transducers;

DETAILED DESCRIPTION

Figure 1:
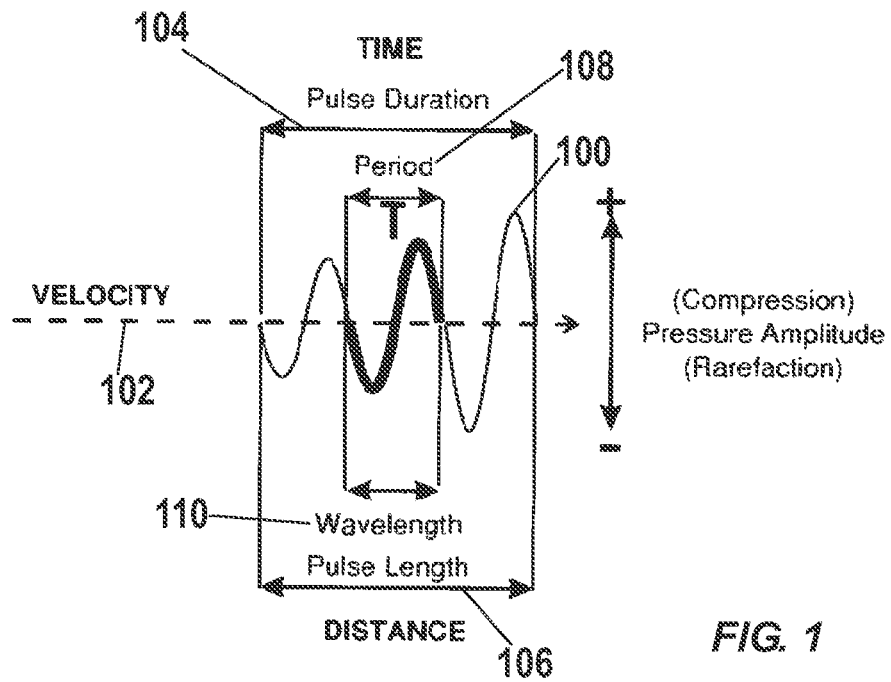
FIG. 1 is a schematic diagram illustrating mechanical wave qualities on both spatial and time scales.
Figure 2:
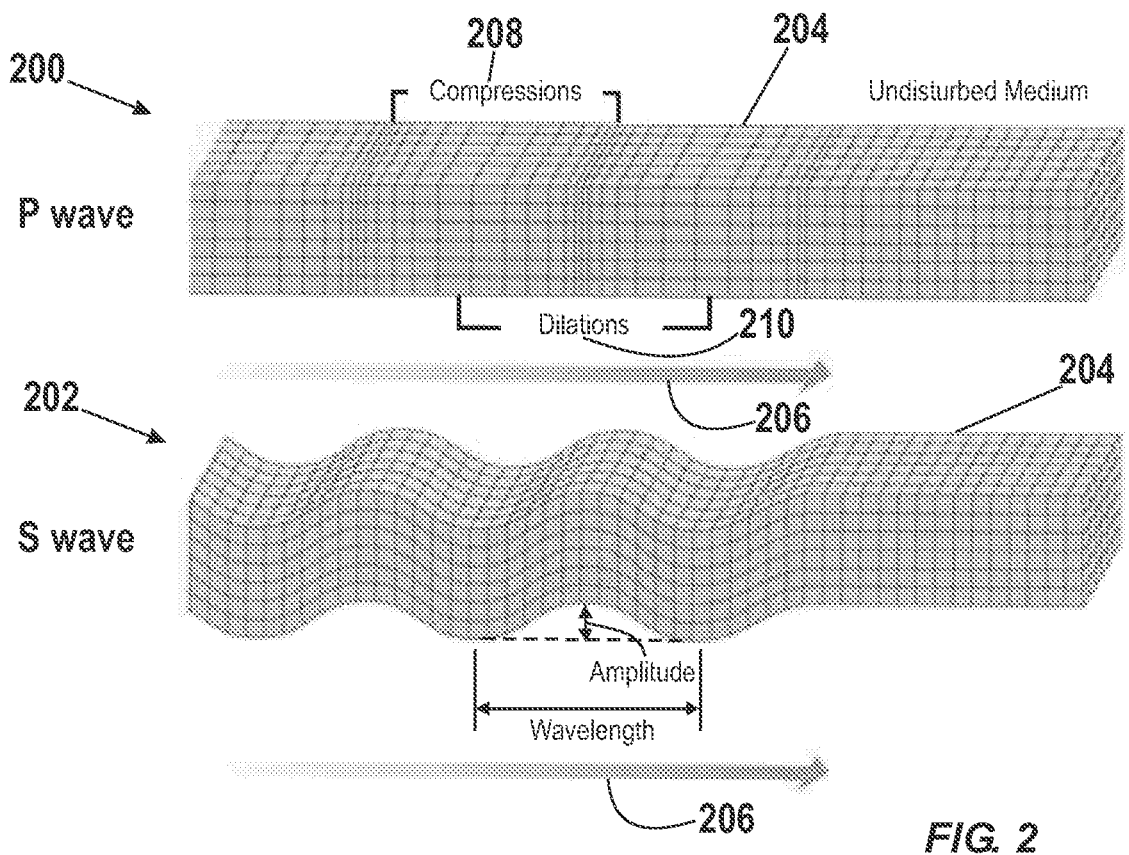
FIG. 2 is a schematic diagram illustrating longitudinal waves and shear waves.
Figure 3C:
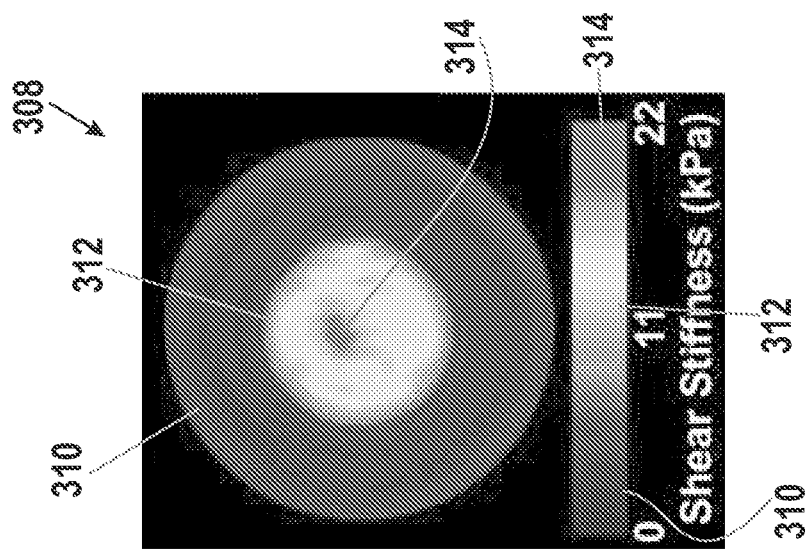
FIG. 3C is an elastogram using 100 Hz mechanical waves and illustrating shear stiffness.
Figure 3B:
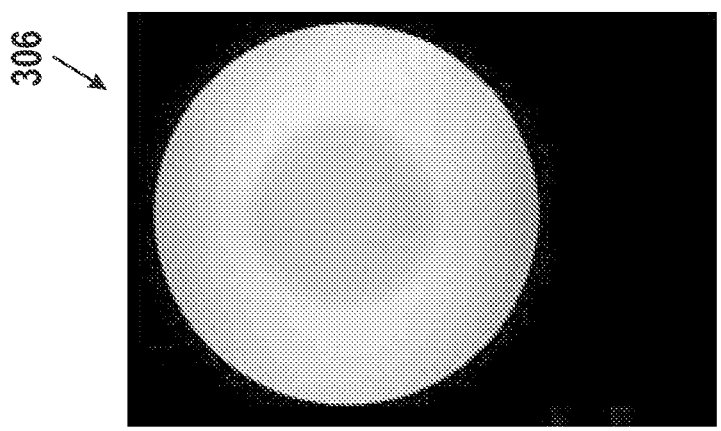
FIG. 3B is an echo planar image using 100 Hz mechanical waves.
Figure 3A:
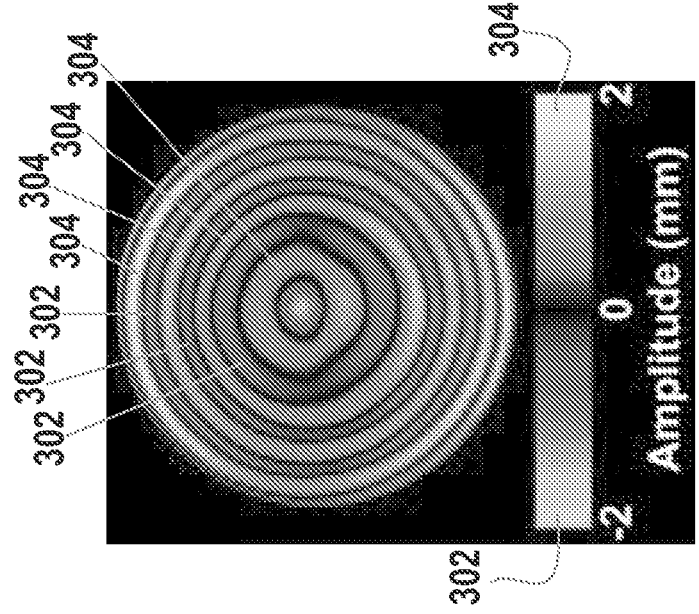
FIG. 3A is an amplitude diagram using 100 Hz mechanical waves and illustrating amplitude of phantom tissue.
Figures 4A, 4B, 4C, 4D:
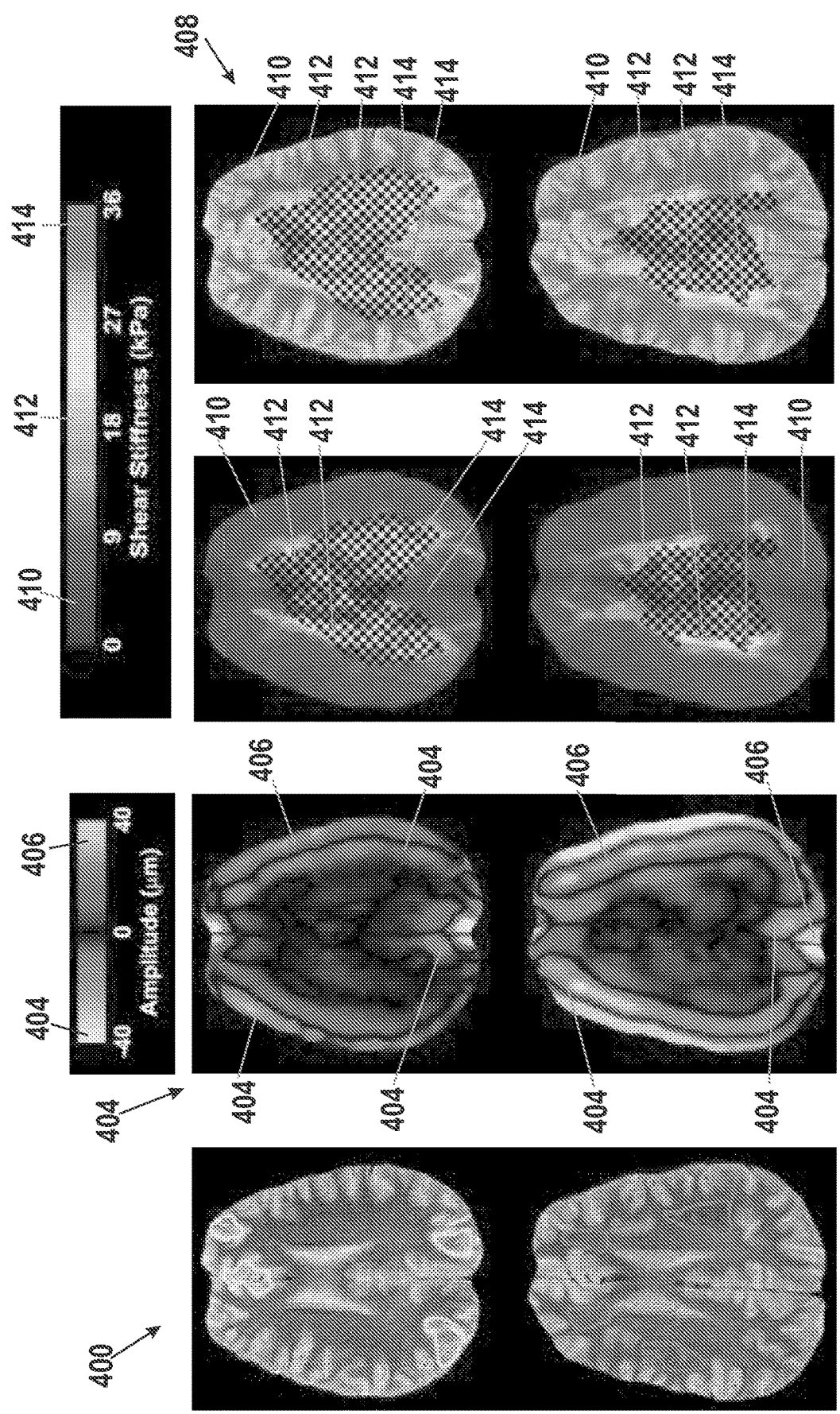
FIG. 4A is an echo planar image of a brain using 100 Hz mechanical waves.
FIG. 4B is an amplitude diagram of a brain using 100 Hz mechanical waves and illustrating amplitude.
FIG. 4C is an elastogram of a brain using 100 Hz mechanical waves and illustrating shear stiffness.
FIG. 4D is the elastogram of FIG. 4C with increased contrast.
Figure 5A:
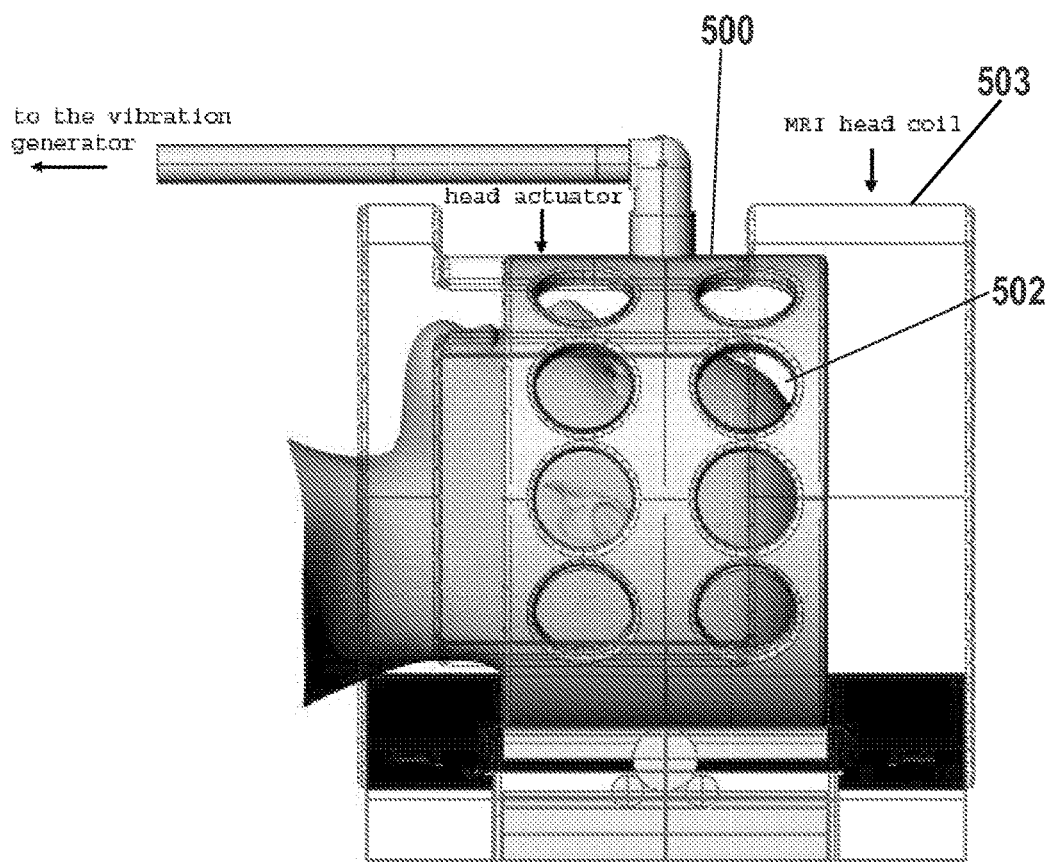
FIG. 5A is a side view of a head actuator for cerebral magnetic resonance elastography subject to being driven by pneumatic devices to displace the entire head of a subject at a frequency range of from about 50 to 2000 Hz, with the actuator being proximate to a MRI head coil.
Figure 5B:
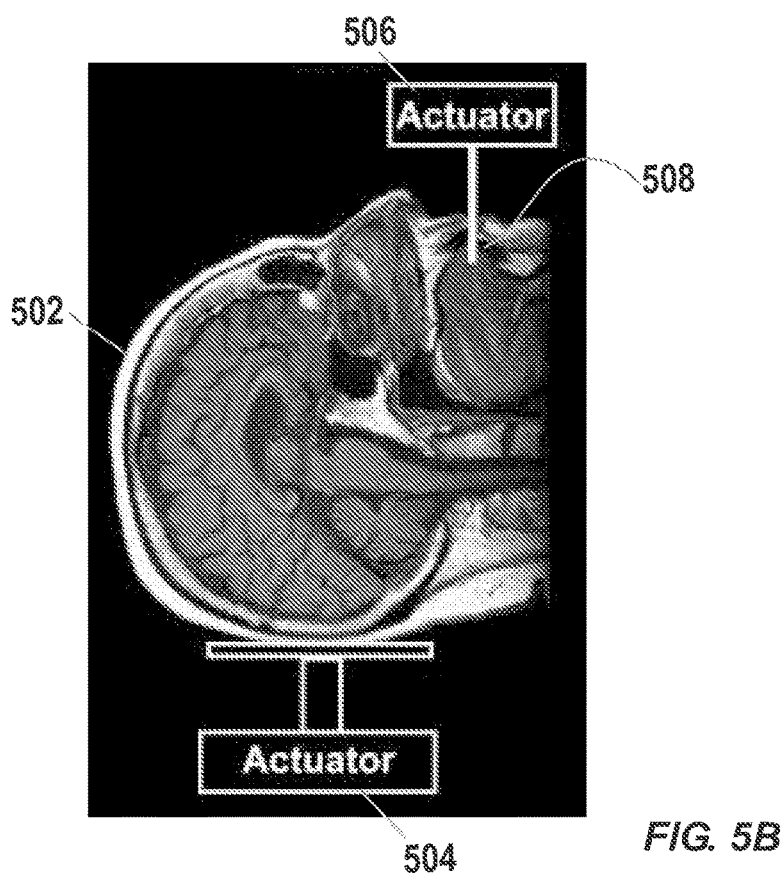
FIG. 5B is a cross-sectional schematic diagram illustrating two different head actuators for cerebral magnetic resonance elastography subject to being driven by pneumatic devices to displace the entire head of a subject at a frequency range of from about 50 to 2000 Hz.
Figure 6A:
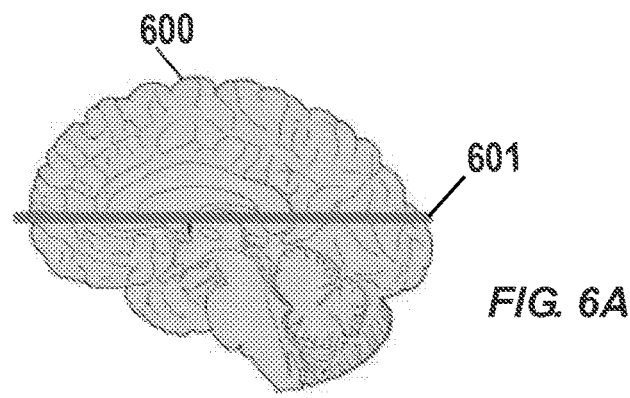
FIG. 6A is a side view of a brain.
Figure 6B:
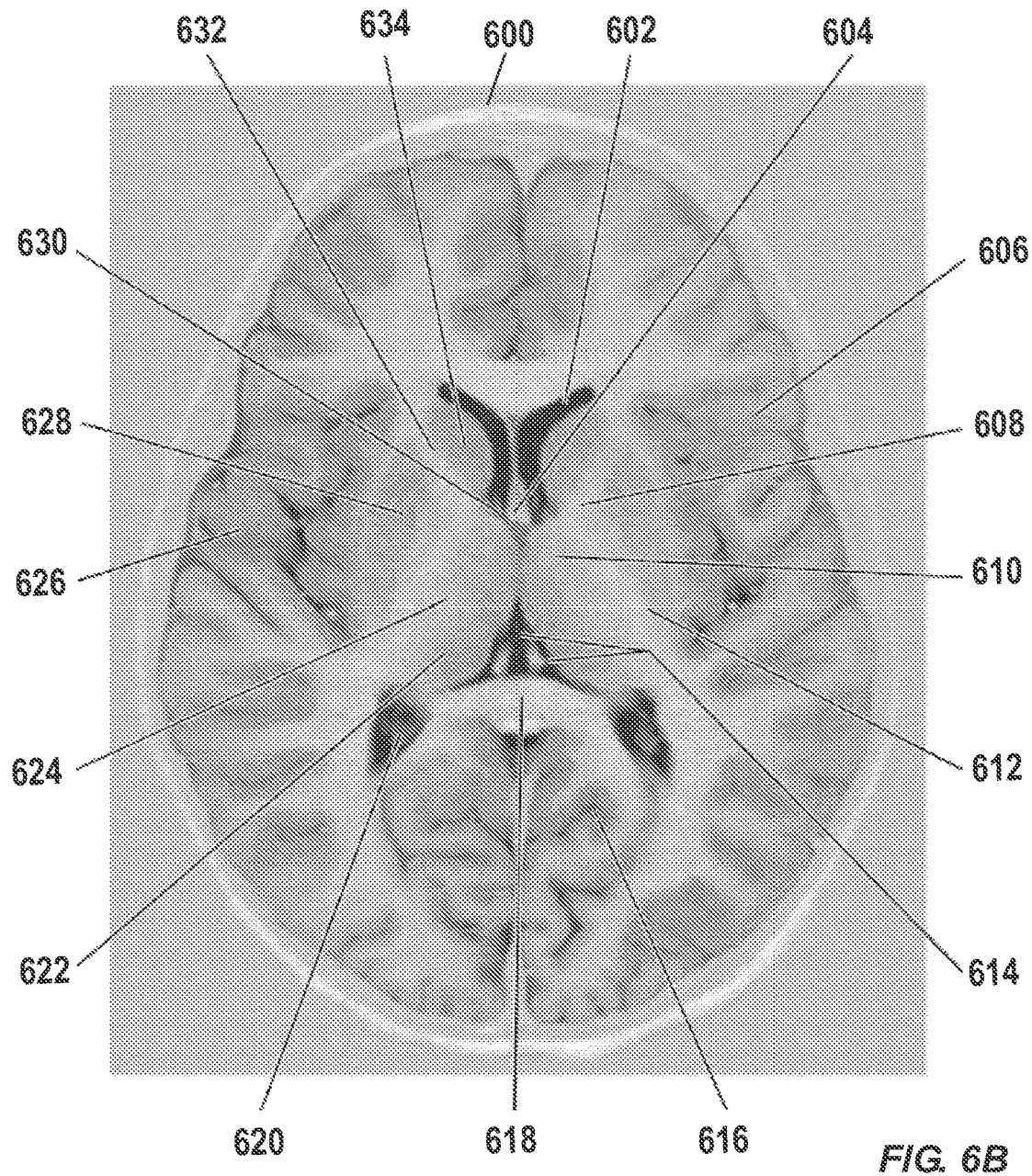
FIG. 6B is a top cross-sectional view of the brain of FIG. 6A taken along a section line shown in FIG. 6A.
Figure 6C:
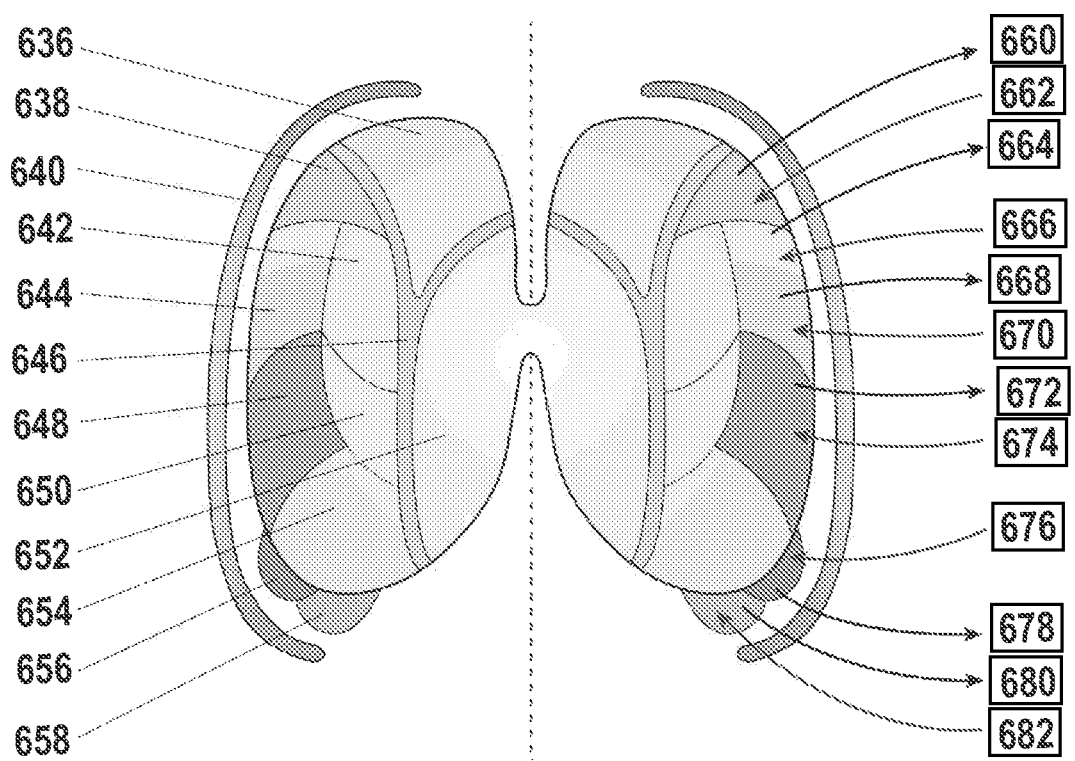
FIG. 6C is a top view of a brain illustrating thalamic nuclei and connections.
Figure 6D:
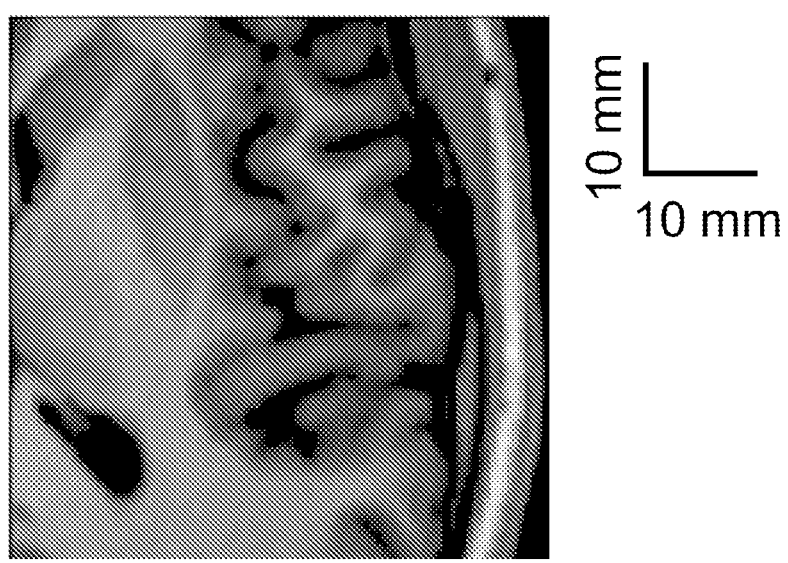
FIG. 6D is a schematic diagram of a portion of a brain illustrating proximity of the ventral lateral and ventral posterior nuclei of the thalamus.

The exemplary embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Disclosed herein is a magnetic resonance elastography (MRE) system and method for generating an elastogram of at least a portion of a brain of a subject. The MRE system includes a computing device in electronic communication with at least one transducer and with a magnetic resonance imaging (MRI) device. In certain embodiments, the at least one transducer includes a single-element ultrasonic transducer or a plurality of transducers. In certain embodiments, a plurality of transducers are configured to concentrate strain resolution at a specific target within the brain tissue. The computing device includes at least one processor and a memory coupled to the at least one processor. The MRE system further includes an MRE engine electronically stored in the memory of the computing device and executable by the at least one processor. The MRE engine is configured to electronically control operation of the at least one transducer to emit ultrasound at a frequency from 0.1 MHz to 1 MHz and with a longitudinal wavelength from 1.54 to 15.4 millimeters to locally displace brain tissue of the subject. In certain embodiments, the ultrasound includes focused ultrasound or planar ultrasound. In certain embodiments, the ultrasound has a cycle time period from 0.5 to 10 milliseconds in brain tissue. In certain embodiments, the at least one transducer is configured to emit the ultrasound for at least one burst having a duration of less than about 500 milliseconds. In certain embodiments, the MRE engine is configured to control operation of the at least one transducer to coordinate emission of ultrasound with one or more biological cycles of the subject. The MRE engine is configured to electronically receive, from the MRI device, at least one signal indicative of measurements of displacement of the brain tissue by the ultrasound. The MRE engine is configured to electronically generate an elastogram of the brain tissue based on the at least one signal. In certain embodiments, the MRE engine is further configured to derive at least one of shear moduli, elastic moduli, or bulk moduli of a brain circuit of the brain tissue.

The spatial wavelength ($\lambda$) of an acoustic wave (see FIG. 1) in a medium is defined as c/f where c is the speed of sound in the medium and f is the acoustic frequency of the sound. As mentioned previously, the speed of sound (c) can be approximated to be about 1540 meters per second in the brain. Thus, for an ultrasound frequency of 100 kHz, the approximate longitudinal wavelength ($\lambda$) will be about 15.4 millimeters and the longitudinal $\lambda$ for ultrasound having an acoustic frequency of 2 MHz will be approximately 0.77 millimeters. Wavelength scales along this range are well suited for modulating mechanical waves in the brain since they approximate the size of many brain nuclei and circuits. Therefore, the present disclosure describes systems and methods for delivering Mesoscopic Wavelength Ultrasound (MWU) having longitudinal waves ranging from approximately 0.77 to 15.4 millimeters in brain tissues to produce micromechanical disturbances of brain nuclei and circuits for characterization of their mechanical properties, such as stiffness, elasticity, rigidity, and viscoelasticity.

The acoustic frequency (f) of ultrasound is defined as the number of ultrasound cycles per second. The period (T) of ultrasound is defined as the time in seconds or milliseconds or microseconds it takes for an ultrasound wave to complete one cycle. The period (T) is defined in time as 1/f. In the present disclosure, systems and methods are described for mechanically disturbing brain tissues using Long-period Ultrasound (LPU) defined as having a T between 0.5 microseconds and about 10 microseconds given an estimation of the speed of sound (c) in brain being roughly 1540 meters per second.

Figure 8A:
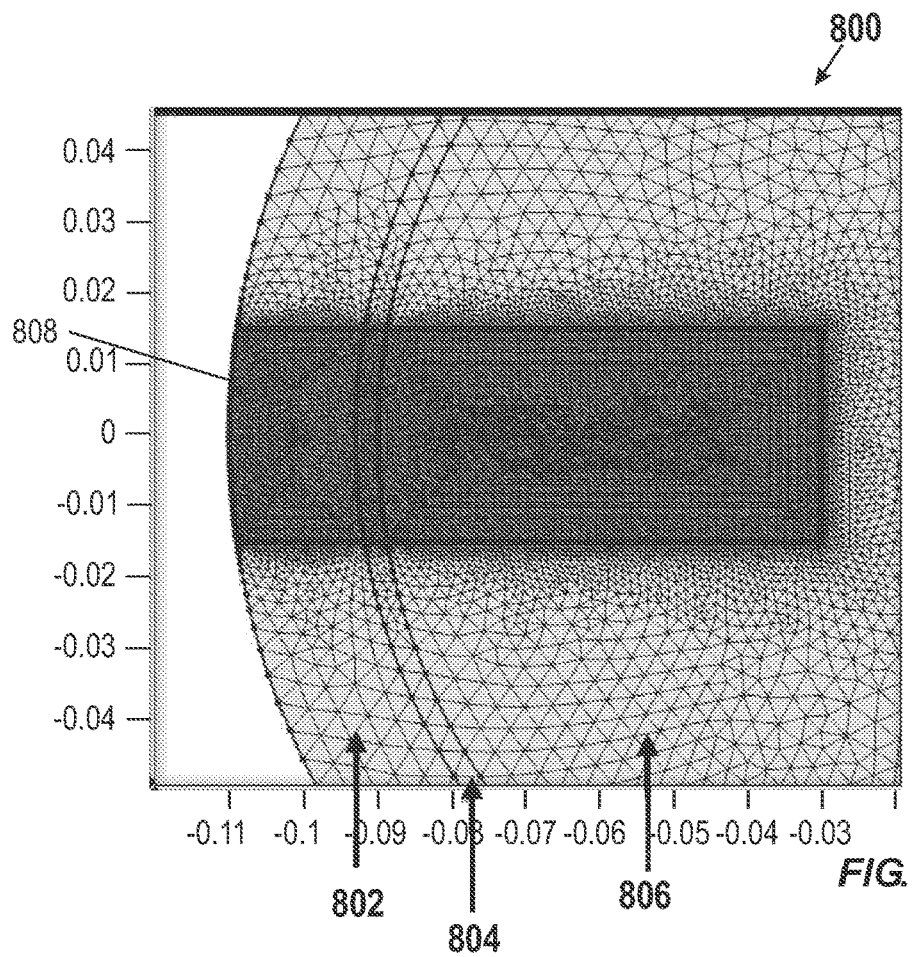
FIG. 8A is a schematic diagram of a cylindrical 2D finite element model approximating the head and brain to model mechanical wave properties and pressure displacement as a function of wave frequency.

Referring to FIG. 8A, to evaluate the spatial resolution attainable in brain tissue perturbed by mechanical pressure waves, a simplified finite element model (FEM) 800 approximating the head as a circle was developed. This FEM had three tissue layers with a skin layer 802, a skull layer 804 (3 millimeters in thickness), and a brain 806 (18 centimeters across). The FEM was exposed to planar (longitudinal) pressure waves 808 having an amplitude of 100 Pascals (Pa) at various acoustic and ultrasonic frequencies.

Figure 8B:
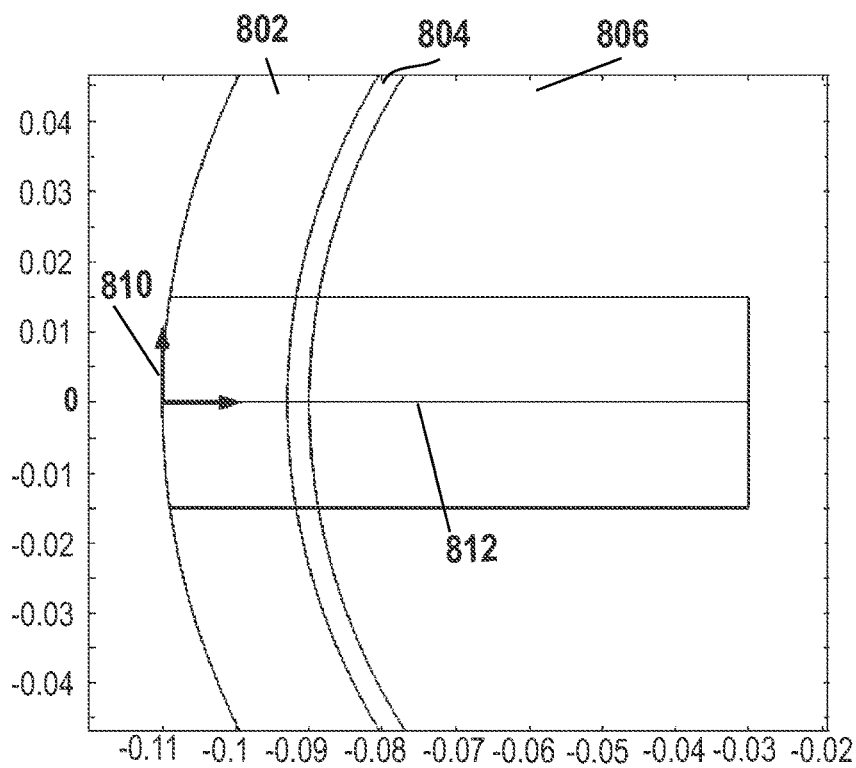
FIG. 8B is a schematic diagram of the model of FIG. 8A with a finely resolved area to extract the pressure profile within the brain along a centerline perpendicular to the incident pressure waves.

Referring to FIG. 8B, within the FEM 800, a finely resolved area was used to extract the pressure profile within the brain along the centerline 810 perpendicular to the incident pressure waves 812.

Figure 8C:
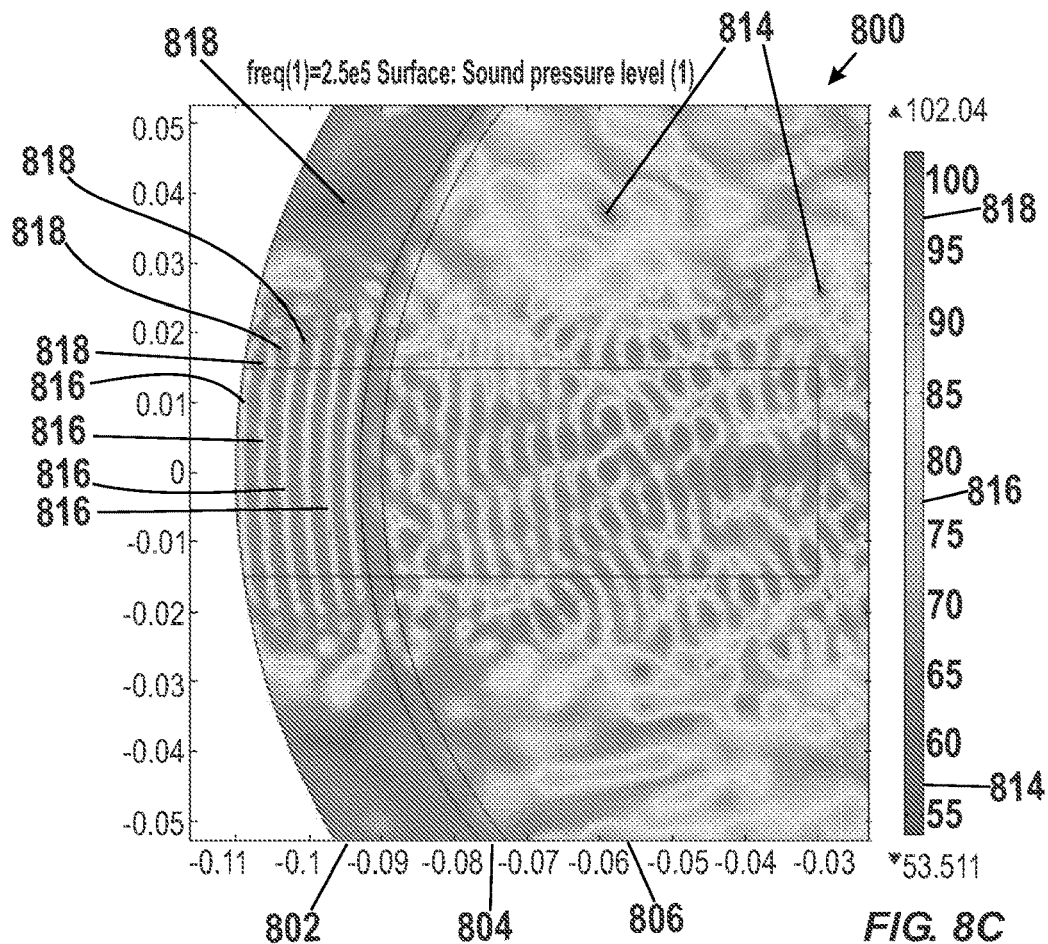
FIG. 8C is a schematic diagram of the model of FIG. 8A illustrating planar mechanical waves constructively and deconstructively interacting with nearby distorted waves.
Figure 8D:
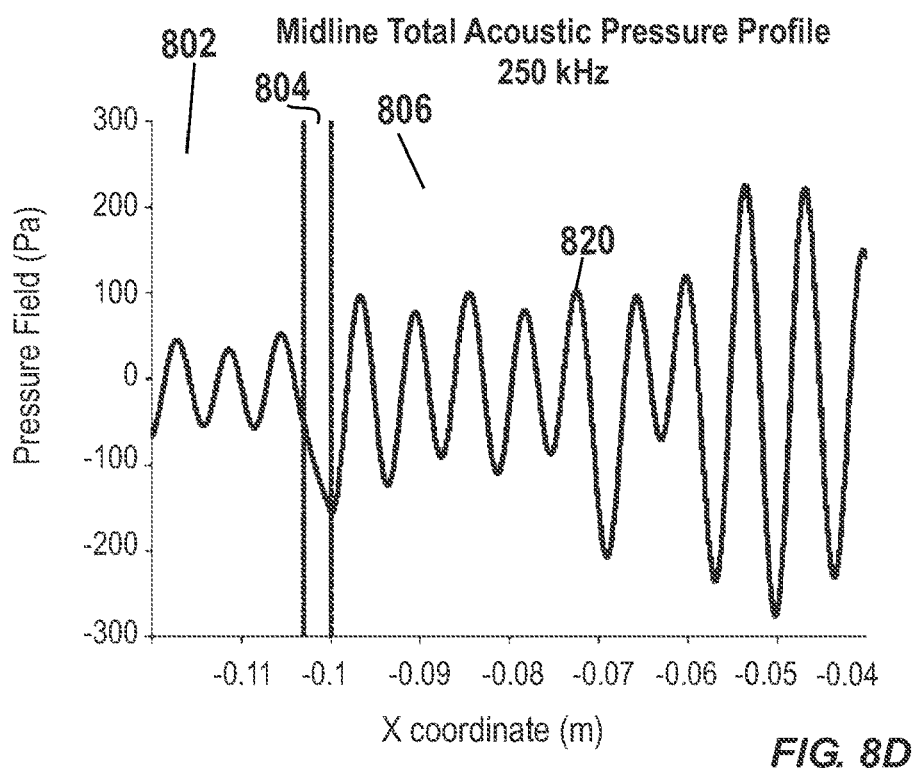
FIG. 8D is a graph of pressure field versus X coordinate illustrating a mechanical wave applied to the model of FIG. 8A propagating across the skull layer and into the brain tissue.

Referring to FIG. 8C, data from this FEM clearly show how incident pressure waves at an acoustic frequency of 250 kHz entering the brain through the skull are distorted by changes in the physical properties of materials and tissues. These planar mechanical waves will constructively and deconstructively interact with nearby distorted waves (see FIG. 8C) (with low sound pressure level (SPL) 814, medium SPL 816, and high SPL 818) as the mechanical wave 820 propagates across the skull layer and into the brain tissue (FIG. 8D).

Figure 9A:
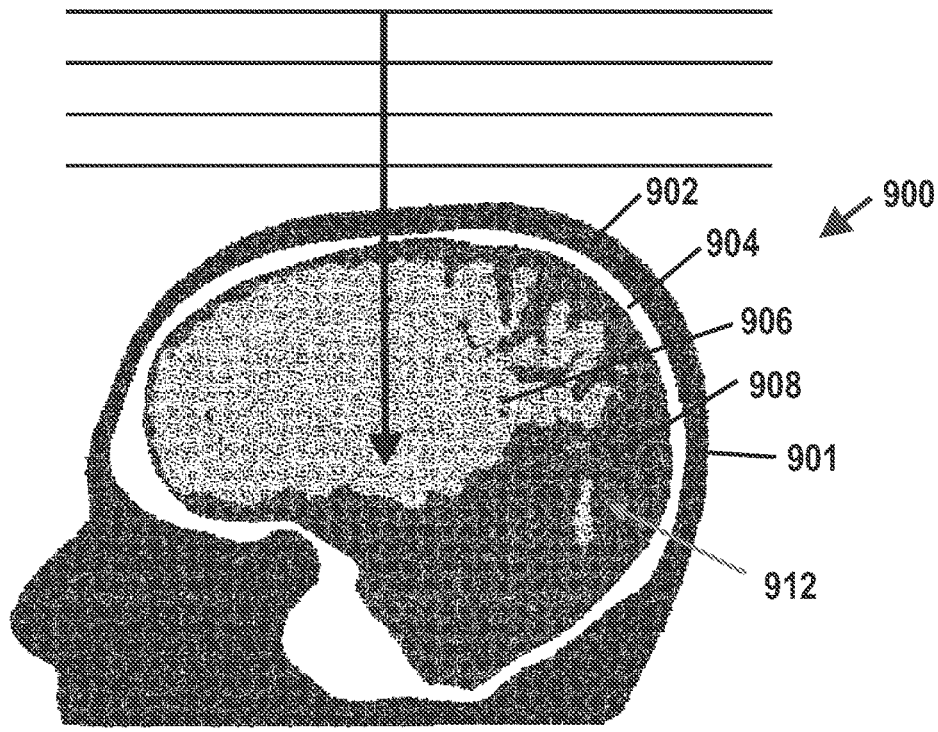
FIG. 9A is a schematic diagram of a 3D finite element model of the skin, skull, cerebrospinal fluid, and brain generated from data obtained from a human volunteer to model mechanical wave properties in the head of a human.

Referring to FIG. 9A, illustrated is a complex three-dimensional, realistic FEM 900 of the human head 901 including skin 902, skull 904, grey matter 906, cerebrospinal fluid 908, and brain layers. The FEM 900 demonstrates the relationship between the frequency of the incident pressure waves 910 and their mechanical resolution in brain tissue 912. The simple cylindrical models of FIGS. 8A-8D can enable observations with respect to the behavior of mechanical waves having mesoscopic wavelengths originating from ultrasound. The realistic FEM 900 can substantiate observations made using the simpler FEMs of FIGS. 8A-8D. In particular, the mechanical resolution properties of brain tissue disturbance waves were found to vary as a function of the longitudinal wavelength ($\lambda$) of the incident mechanical waves delivered by Mesoscopic Wavelength Ultrasound (MWU).

Figure 9B:
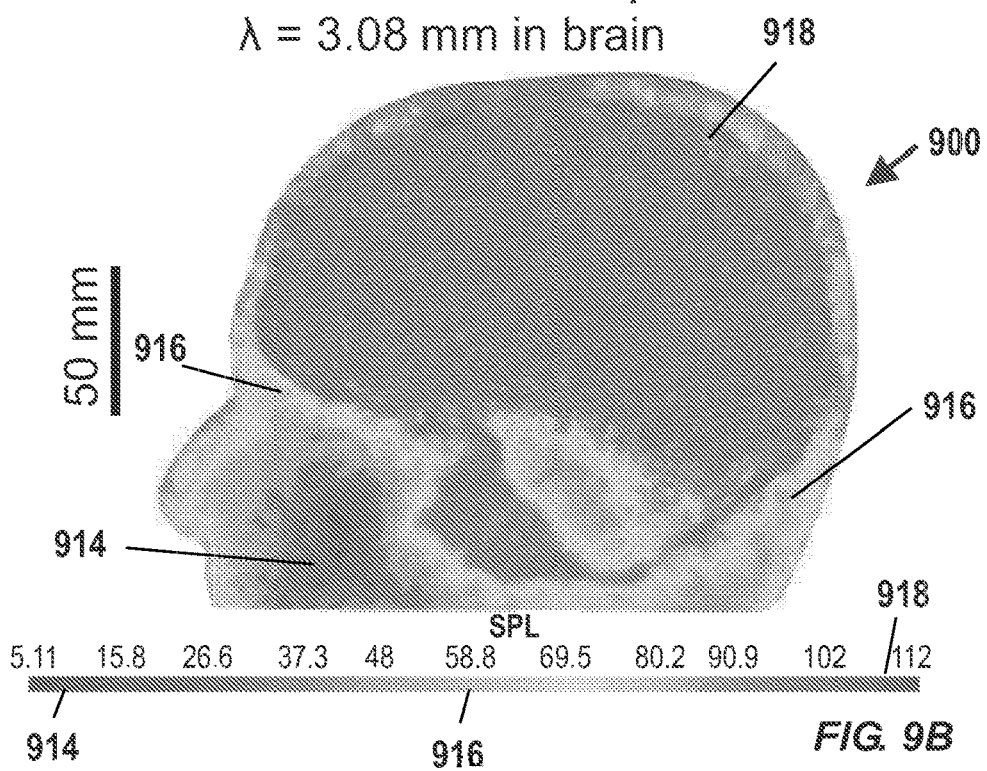
FIG. 9B is an elastogram of the 3D finite element model of FIG. 9A with an applied frequency of 0.5 MHz.
Figure 9C:
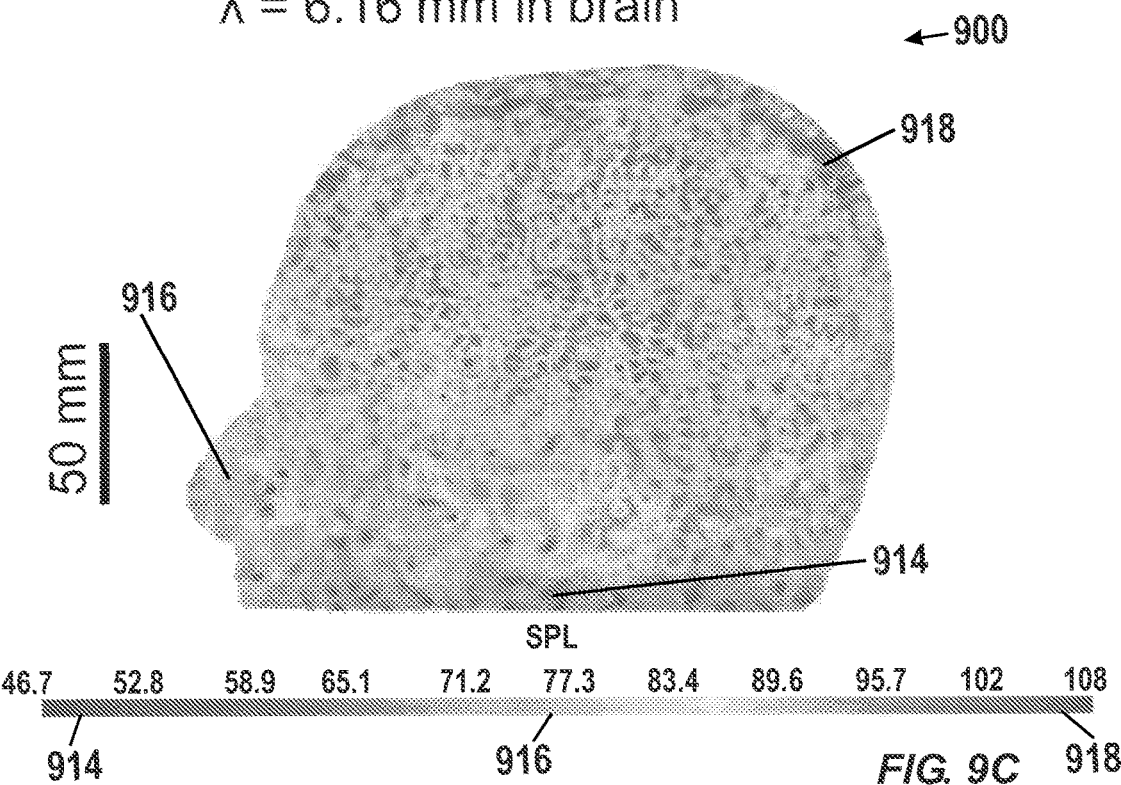
FIG. 9C is an elastogram of the 3D finite element model of FIG. 9A with an applied frequency of 0.25 MHz.
Figure 9D:
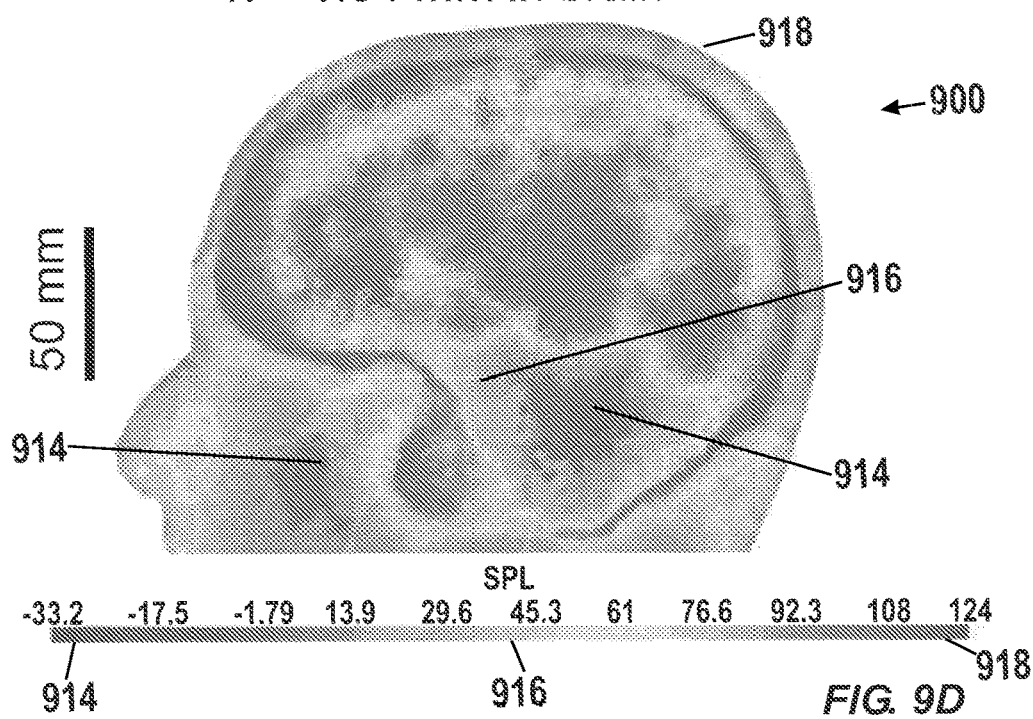
FIG. 9D is an elastogram of the 3D finite element model of FIG. 9A with an applied frequency of 1.0 MHz.
Figure 9E:
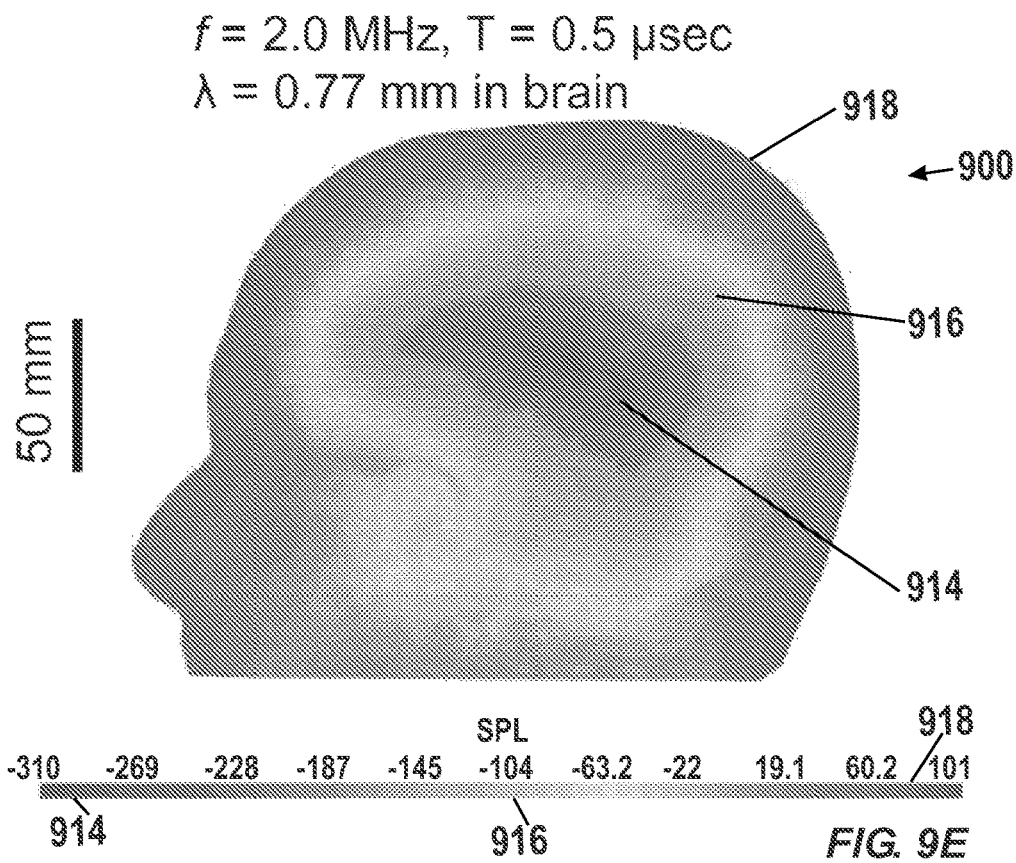
FIG. 9E is an elastogram of the 3D finite element model of FIG. 9A with an applied frequency of 2.0 MHz.
Figure 9F:
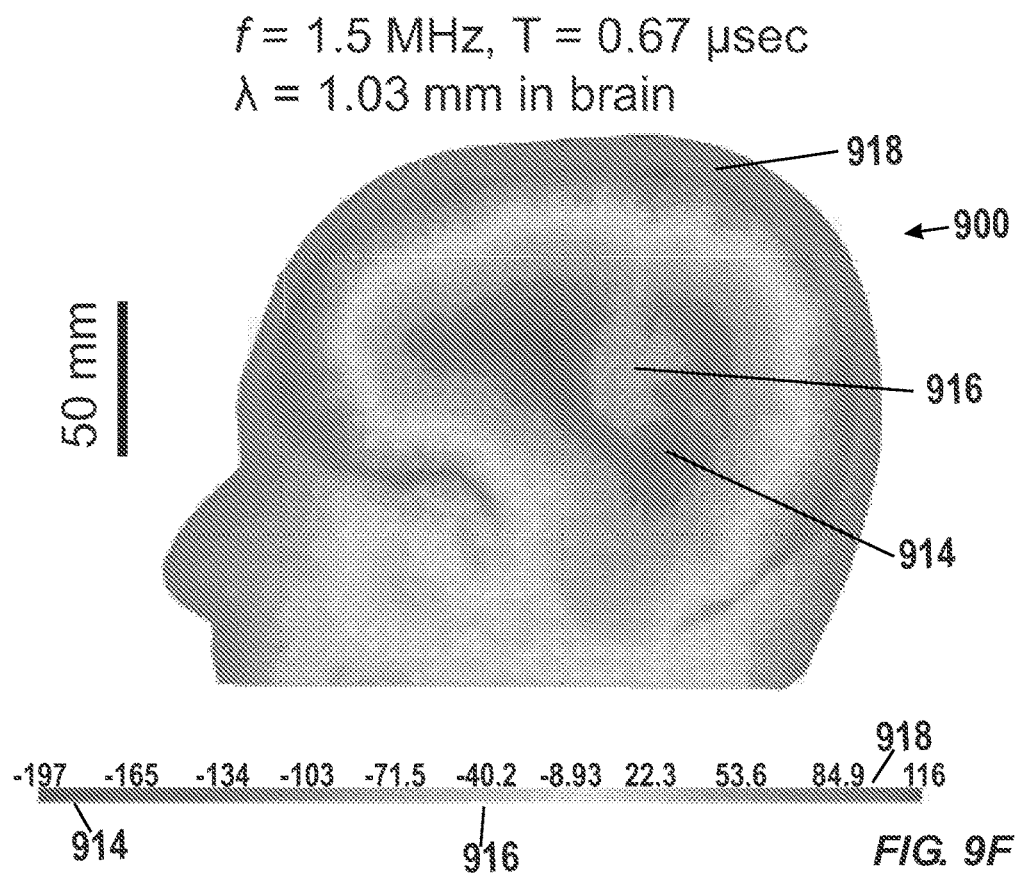
FIG. 9F is an elastogram of the 3D finite element model of FIG. 9A with an applied frequency of 1.5 MHz.

As illustrated in FIGS. 9B-9F, simulations were run by transmitting MWU having a $\lambda$ in brain tissue 912 ranging from about 0.77 and 6.16 millimeters at acoustic frequencies from about 2.0 MHz to 0.25 MHz, respectively. Each of FIGS. 9B-9F has areas of low SPL 914, medium SPL 916, and high SPL 918. FIG. 9B had a f of 0.5 MHz, T of 2 μsec, and $\lambda$ of 3.08 mm in brain tissue. FIG. 9C had a f of 0.25 MHz, T of 4 μsec, and $\lambda$ of 6.16 mm in brain. FIG. 9D had a f of 1.0 MHz, a T of μsec, and a $\lambda$ of 1.54 mm in brain tissue. FIG. 9E had a f of 2.0 MHz, a T of μsec, and a $\lambda$ of 0.77 mm in brain tissue. FIG. 9F had a f of 1.5 MHz, a T of 0.67 μsec, and a $\lambda$ of 1.03 mm in brain tissue.

Figure 7A:
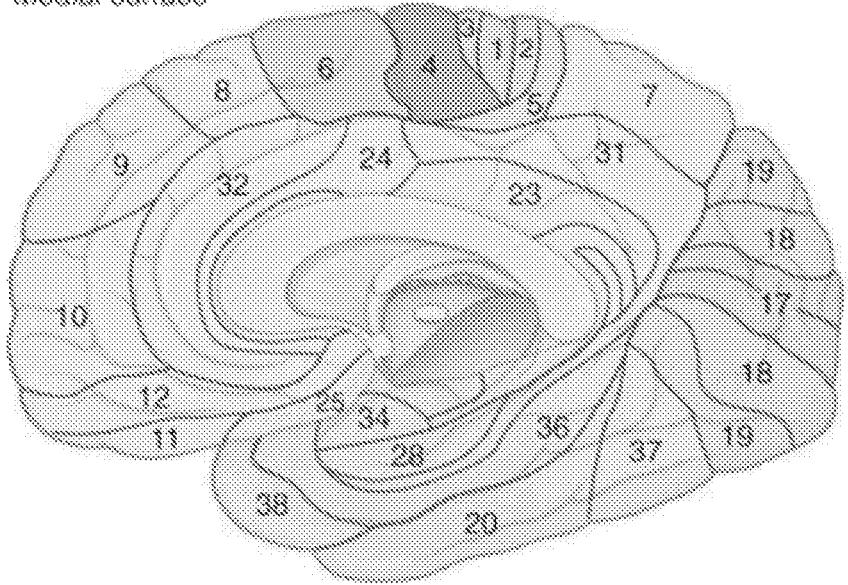
FIG. 7A is a schematic diagram of a medial surface of a brain and subdivision of the brain into anatomically specialized regions using Broadmann's areas.
Figure 7B:
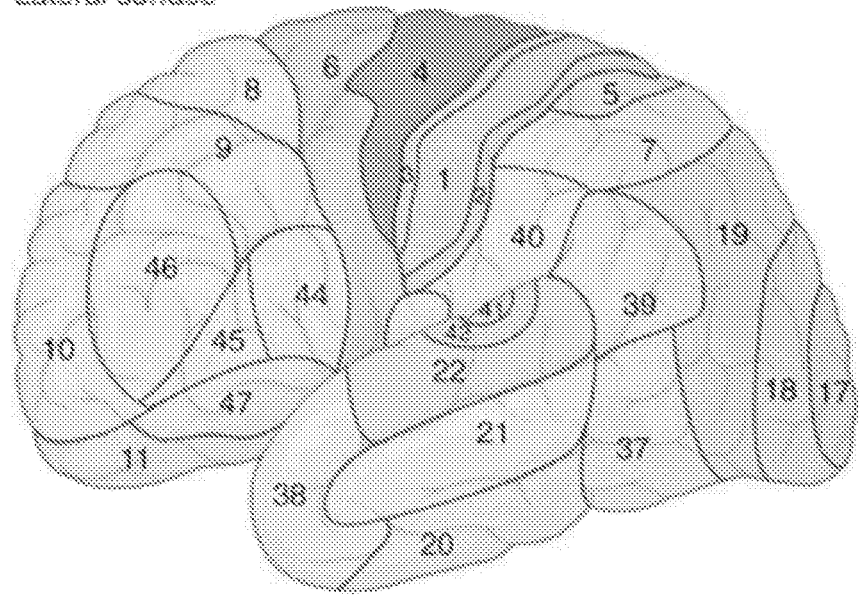
FIG. 7B is a schematic diagram of a lateral surface of a brain and subdivision of the brain into anatomically specialized regions using Broadmann's areas.

Referring to FIG. 9B, data from these simulations show how MWU having a longitudinal $\lambda$ of about 6.16 millimeters in brain tissue can generate structured patterns of mechanical pressure nodes. Comparatively, referring to FIG. 7F, shorter wavelength MWU having a $\lambda$ of about 0.77 millimeters in brain tissue is rapidly attenuated as a function of depth in the brain, as well as becomes predominately lost in the skin, skull, and superficial brain layers. Data from studies performed by the inventor(s) indicate the mean optimal $\lambda$ for mechanically disturbing brain circuits with transcranial MWU is on a range from about 1.54 to 15.4 millimeters, corresponding to acoustic frequencies of about 1 to 0.1 MHz respectively.

Figure 10A:
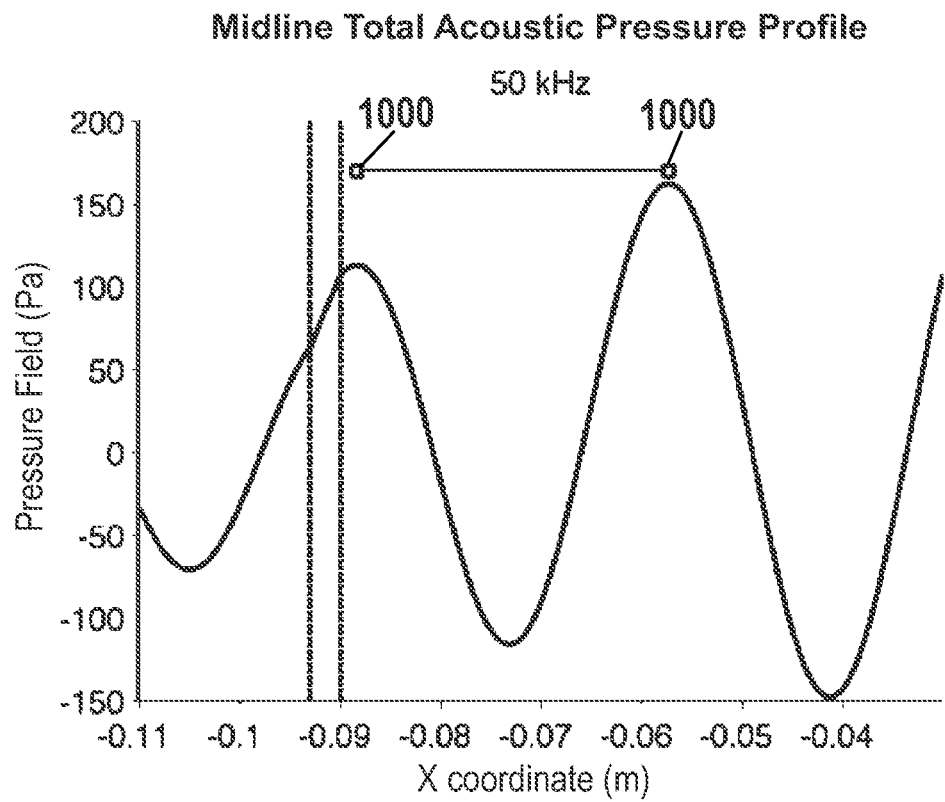
FIG. 10A is a graph of pressure field versus X coordinate illustrating spatial resolution of mechanical waves at ultrasonic frequencies 50 kHz as a lateral pressure displacement profile simulated using a FEM of brain tissue.
Figure 10B:
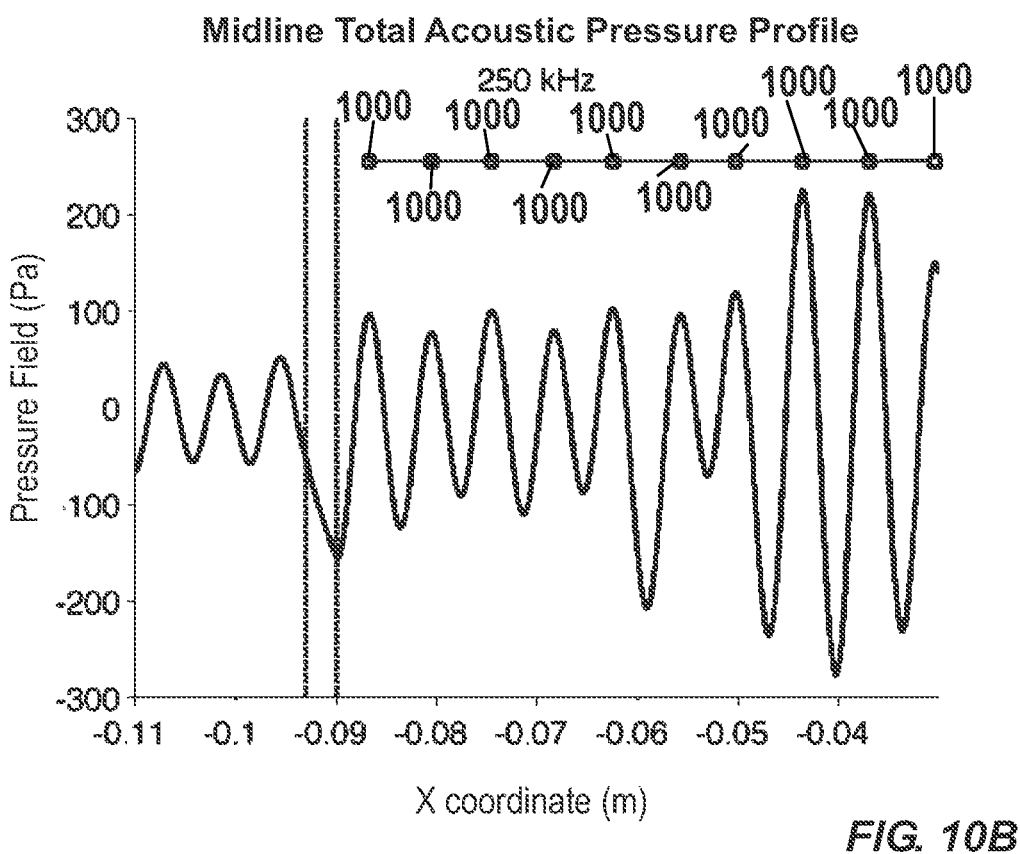
FIG. 10B is a graph of pressure field versus X coordinate illustrating spatial resolution of mechanical waves at ultrasonic frequencies 250 kHz as a lateral pressure displacement profile simulated using a FEM of brain tissue.
Figure 10C:
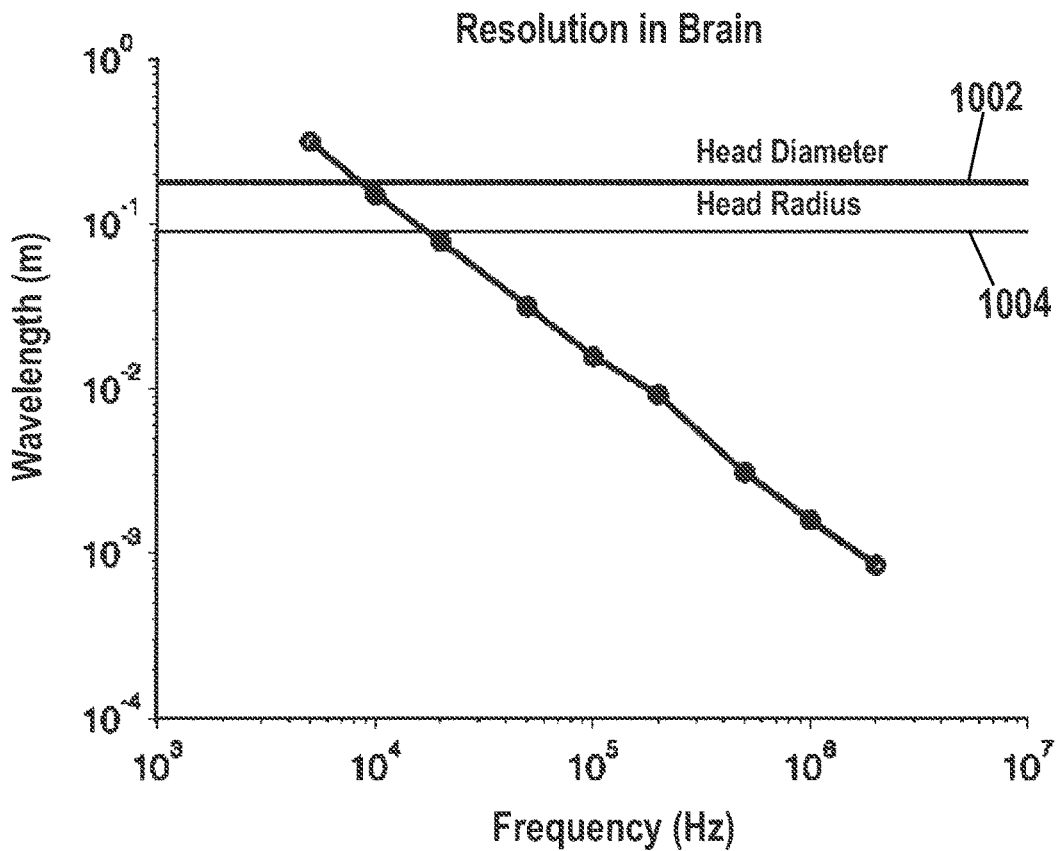
FIG. 10C is a graph of wavelength versus frequency illustrating brain resolution for the model of FIGS. 9A-9F.
Figure 10D:
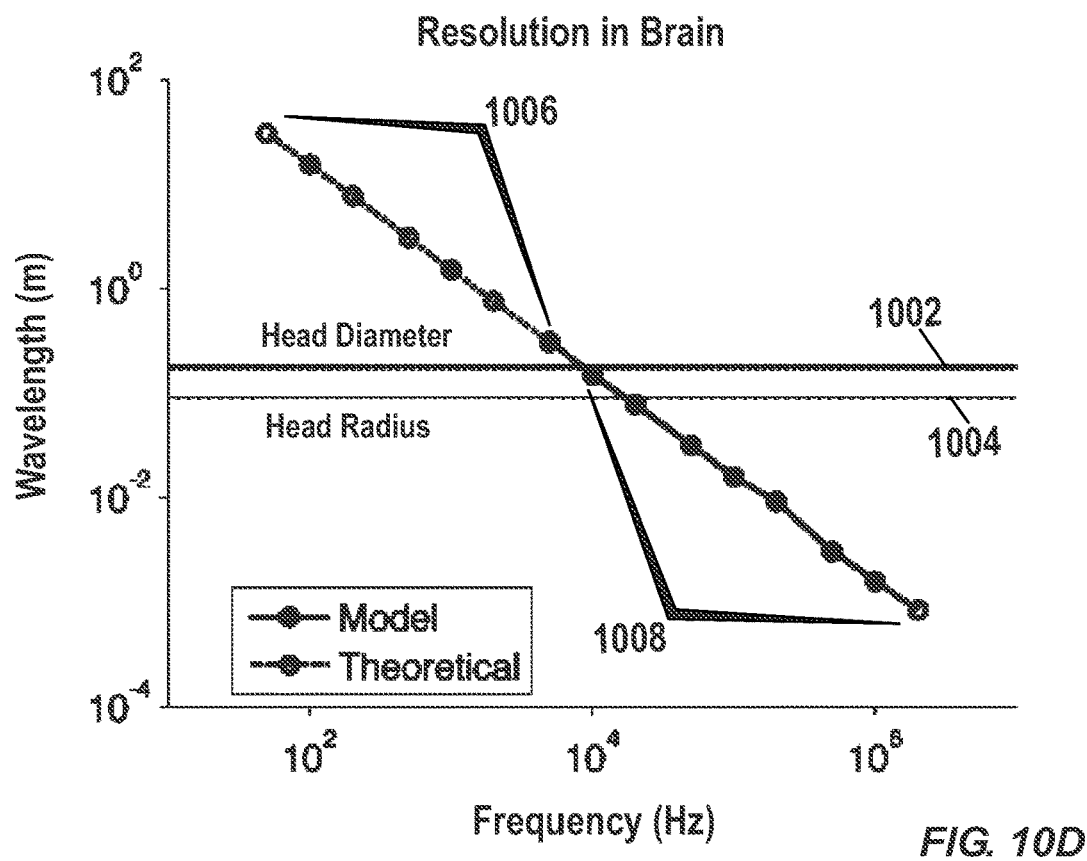
FIG. 10D is a graph of wavelength versus frequency illustrating brain resolution for the model of FIGS. 8A-8D, including modeled and theoretical values.

Referring to FIGS. 10A-10C, this is further supported by the data obtained using the cylindrical FEM of FIGS. 8A-8D. In this cylindrical model, isolating the pressure profile along the centerline readily allows the determination of the wavelength within the tissue. Shown are the pressure profiles for 50 kHz (FIG. 10A) and 250 kHz (FIG. 10B) and their corresponding measurements of wavelength by identifying the peaks 1000 of the pressure profiles. The resultant wavelength of the pressure wave in tissue at a range of frequencies between 50 Hz and 2 MHz is shown in FIG. 10C with the head diameter 1002 and radius 1004 (note the use of logarithmic scales). FIG. 10D includes the theoretical values 1006 and the model values 1008. As can be observed from these modeling studies, there may be a need for relatively high frequencies of actuation (as compared to the typical 60 to 100 Hz used for cerebral magnetic resonance elastography (MRE)) to achieve a resolution of mechanical deformation smaller than the dimensions of the head and encapsulated brain nuclei and circuits. Therefore, the present disclosure describes the use of MWU for mechanically disturbing brain circuits to characterize mechanical properties of their tissues using various elastographic imaging approaches.

Figure 11C:
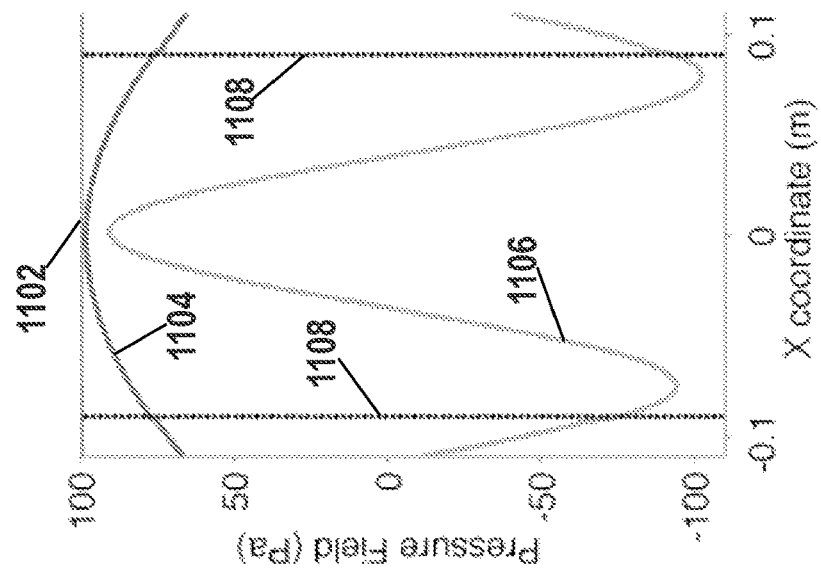
FIG. 11C is a graph of pressure field versus X coordinate illustrating a head pressure profile for a pressure field between −100 and 100 Pa.
Figure 11B:
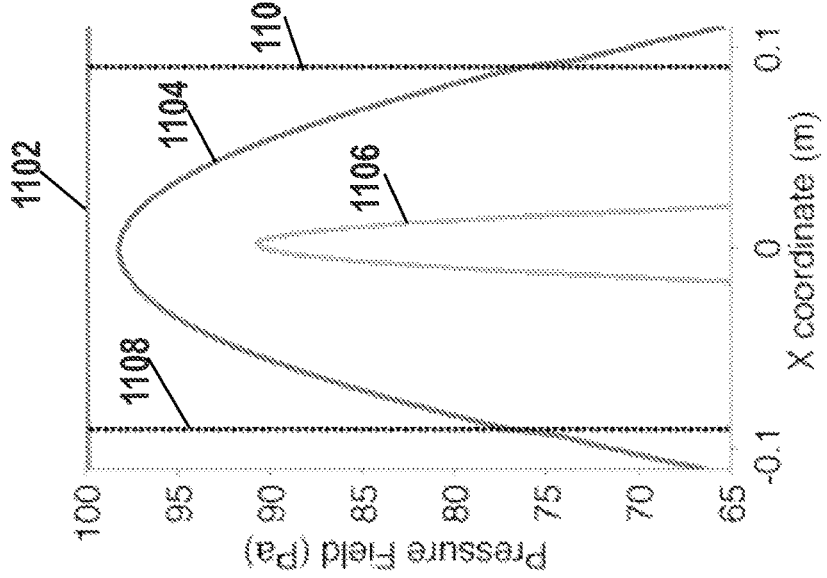
FIG. 11B is a graph of pressure field versus X coordinate illustrating a head pressure profile for a pressure field between 65 and 100 Pa.
Figure 11A:
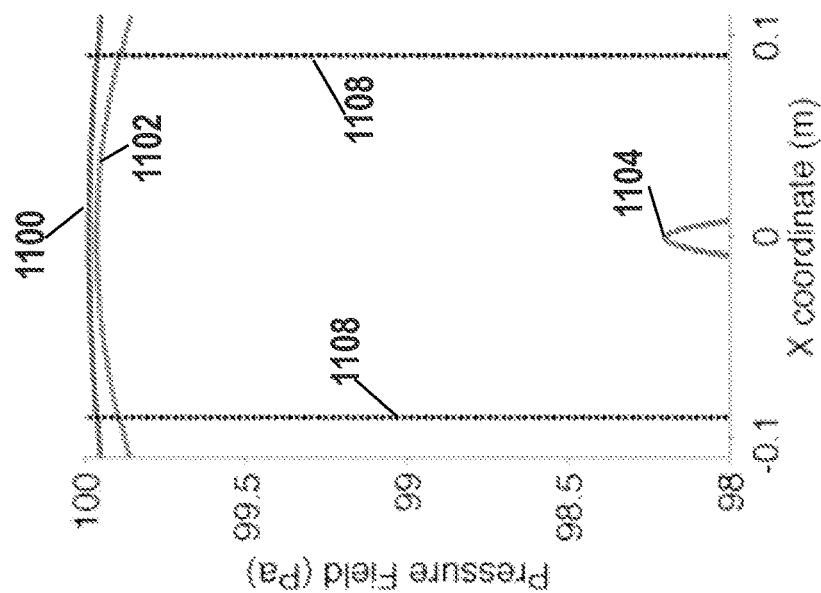
FIG. 11A is a graph of pressure field versus X coordinate illustrating a head pressure profile for a pressure field of between 98 and 100 Pa.

Referring to FIGS. 11A-11C, typical actuating or tissue displacement frequencies used in conventional cerebral MRE include 60 Hz 1100, 100 Hz 1102, and 1800 Hz 1104. The pressure profiles for these frequencies, in addition to 10 kHz 1106, are shown in FIG. 9A, where an incident pressure wave of 100 Pa is utilized for all frequencies. The wavelength of conventional MRE actuating frequencies may be larger than the dimensions of the head, which can be indicated in FIG. 9A by the vertical dashed lines 1108. In addition, the amplitude of these lower frequency pressure waves can attenuate with increasing frequency (take note of the differences in y-scales in A, for example). For conventional cerebral MRE actuators, there may be a limited range of power available to comfortably actuate the cerebral tissue, as well as to reliably drive the actuator. The trade-off between delivering mechanical energy to the brain needs to be balanced along with the attenuation through tissue. In the case of ultrasound and in particular MWU, this may be less of a concern, due to the use of power electronics and the physics underlying interaction of pressure waves within the tissue made possible by their shorter wavelengths. As the wavelengths for conventional lower frequencies of actuation that were not determined within the computational model, they were calculated for an infinite medium having the same gross mechanical properties of brain using c/f, where c is the speed of sound in the brain (about 1540 meters per second) and f is the frequency of actuation. These results are included with the observed wavelengths in the computational model in FIG. 9B. Again, take note of the logarithmic axes in FIG. 9B and how the spatial resolution of deformations are larger than the dimensions of the head for frequencies below approximately 10 kHz, for example.

As explained above, low-frequency mechanical waves (50 to 2000 Hz) may not be suited for achieving appropriate spatial resolutions in brain circuit elastography, but high acoustic frequencies (>2 MHz) can also suffer limitations. The attenuation of mechanical pressure delivered by ultrasound can vary across distance as a function of frequency and tissue or media density, where intensity loss is about 0.2 to 0.5 dB/cm/MHz. In soft tissues, therefore, an attenuation factor of 0.5 dB/cm/MHz can be used to estimate the loss of an ultrasound pressure to be 0.05 dB/cm at 0.1 MHz, 0.5 dB/cm at 1 MHz, 1 dB/cm at 2 MHz, and 5 dB/cm at 10 MHz. Deep-brain circuits such as the thalamus and other subcortical nuclei reside about 5 to 10 centimeters (cm) beneath the brain surface. One could expect an attenuation of about 5 to 10 dB (not considering loss due to skull bone or other tissue interfaces) when targeting deep-brain circuits located 5 to 10 cm deep using 2 MHz ultrasound, but only 0.625 to 1.25 dB attenuation when targeting the same circuits with 0.25 MHz ultrasound. Similar attenuation behaviors can be observed in data obtained from FEM simulations using 0.25 MHz (FIG. 9B) and 2 MHz ultrasound (FIG. 9F).

As previously described, acoustic radiation force imaging (ARFI), shear wave elasticity imaging (SWEI), supersonic shear imaging or shear wave imaging (SWI), and other ultrasound imaging-based approaches to elastography rely on ultrasound to displace tissues at acoustic frequencies typically 2 MHz or higher. For displacements and elastographic imaging of soft tissues, such as the breast or liver, such approaches are not problematic and represent some advantages in terms of the ability to image at high frame rates. However, in cases where soft tissues are protected by bone, such as the case of the brain, one must consider the ability of ultrasound to be transmitted through bone. In fact, the mean optimal gain for the transcranial transmission and brain absorption of ultrasound has been shown to occur at acoustic frequencies <0.65 MHz, as demonstrated by the FEM data in FIGS. 9A-9F. Thus, for conducting tissue displacements of brain tissues using transcranially delivered ultrasound, one should implement acoustic frequencies less than 1 MHz, and even more preferably <0.65 MHz. However, acoustic frequencies up to 2 MHz may be appropriate for superficial targeting. One must keep in mind the attenuation of ultrasound increases as acoustic frequency increases as discussed above. Therefore, when considering the attenuation properties, transmission characteristics, and mechanical wavelengths of ultrasound, it appears that acoustic frequencies between 0.1 MHz and 2 MHz are nearly ideal for tissue actuation or displacement used in estimating the shear, elastic, and bulk moduli of brain circuits and nuclei when combined with elastographic imaging methods.

Systems, methods, and devices of the present invention utilize mesoscopic wavelength ultrasound composed of longitudinal waves ranging from approximately 0.77 to 15.4 millimeters in brain tissues to produce micromechanical disturbances of brain nuclei and circuits for characterization of their mechanical properties, such as stiffness, elasticity, rigidity, and viscoelasticity. Systems, methods, and devices are described for mechanically disturbing or displacing brain tissues using Long-period Ultrasound (LPU) defined as having a period (T; 1/f) between 0.5 microseconds and about 10 microseconds given an estimation of the speed of sound (c) in brain being roughly 1540 meters per second.

Systems, methods, and devices comprise an ultrasound device operably attached or associated to the a body part, wherein the ultrasound device may comprise one or more components for generating ultrasound waves (such as ultrasonic emitters, transducers, piezoelectric transducers, piezopolymer transducers, composite transducers, CMUTs (capacitive micromachined ultrasound transducers), and may be provided as single or multiple transducers (optionally in an array configuration). Ultrasound transducer elements may use focusing lenses such as simple lenses, lens arrays, acoustic hyperlenses or metamaterials in order to localize the disturbance or displacement of central nervous system tissues including the brain. Optionally, the ultrasound device or system may comprise power sources, components for transmitting or receiving data, components for remote activation of the ultrasound generators, body positioning components, and/or other location or tracking devices. The ultrasound waves provided may be of any amplitude or shape, and may be focused or unfocused, depending on the region of the central nervous system or brain being targeted. Mesoscopic wavelength ultrasound or LPU may be delivered to disturb central nervous system tissues in waveforms having peak pressures at the site of tissue being targeted ranging from about 10 kiloPascals (kPa) to about 5 MegaPascals (MPa). Such MWU or LPU waveforms may have spatial-peak pulse-average intensities of about 100 mW/cm$^2$ to about 1000 W/cm$^2$.

Systems, devices, and methods according to certain embodiments involve mechanically disturbing, displacing, or compressing central nervous system tissues including the brain by providing ultrasound waves to the body, or particular regions of the body (such as the head), at an effective intensity and for an effective time range so that the neural or brain tissue is displaced sufficiently to generate shear waves. It is contemplated that an ultrasound device or system that is operably attached to the subject (such as an ultrasound device comprising a helmet, cap, or other head mounted device, or translational mechanical device comprising at least ultrasound generating components), may be used to provide the MWU or LPU exposures described herein. Such ultrasound methods and treatments described herein may also be provided to a subject using ultrasound components that are not incorporated into a wearable device, but are attached directly to the subject or are at some physical distance from the subject.

Methods of the present disclosure may comprise disturbing, displacing, or compressing central nervous system or brain tissues in a subject by providing an effective amount of at least ultrasound waves to one or more body structures, for example, by using an ultrasound device coupled to the head, a system for characterizing neuronal viscoelasticity, disclosed herein. An exemplary method may comprise estimating the shear modulus, elastic modulus, or complex modulus of brain circuits or brain nuclei affected by trauma or disease. Methods of the present invention may include providing an effective amount of MWU or LPU to the brain of a subject or subject that is diseased or has received trauma or to a surrounding brain regions. Methods of the present invention may comprise combinations of steps of the methods taught herein, and wherein ultrasound is provided by an ultrasound device disclosed herein. Methods may be accomplished utilizing ultrasound devices.

FIG. 12 is a diagram illustrating use of at least a portion of an MRE system. The MRE system 1200 includes at least one transducer 1202 attached to a head of a subject to deliver MWU 1204 to a target region 1206 of a brain 1208 of a subject to cause local tissue disturbance, tissue strain, and/or shear waves. In certain embodiments, devices for and methods of delivering LPU or MWU include at least one ultrasound transducer, a power amplifier, a function generator or digitized stimulus waveform, a synchronizing triggering circuit, and an imaging array for encoding tissue strain, displacement, or deformation or for detecting shear wave propagation speeds.

In certain embodiments, the ultrasound emitted by the transducer has a power limit of a maximum of 100 watts, and in certain embodiments, in a range of from 100 to 500 milliwatts. In certain embodiments, a gel (e.g., silicone and/or hydrogel, etc.) may be applied to the transducer, such that it is placed between the transducer and the subject.

Systems for and methods of delivering LPU or MWU for mechanical displacement of brain tissues them rely on one or more ultrasound transducers. Referring to FIG. 13A, in some embodiments, a single-element planar or focused ultrasound transducer 1300 having a diameter of about 20 to 50 millimeters and a center frequency of 0.5 MHz is used to provide MWU having a longitudinal λ in brain of about 3.08 millimeters to regions of the motor or somatosensory cortex for locally displacing the targeted brain tissue for characterizing its shear modulus (G), elastic modulus (E), or bulk modulus (K). In related embodiments, specific nuclei or regions of the prefrontal cortex, motor cortex, hippocampus, cerebellum, thalamus, basal ganglia, somatosensory cortex, visual cortex, and other brain regions can similarly be targeted and displaced with ultrasound to estimate their mechanical properties using known elastographic imaging approaches.

Referring to FIG. 13B, in other embodiments, two single-element planar transducers 1302(1), 1302(2) can be positioned on and acoustically coupled to the head to bilaterally target two different brain regions simultaneously (in parallel) or serially (in sequence). In such an example, the right primary motor cortex may be targeted for mechanical disturbance using MWU at the same time the left dorsolateral prefrontal cortex is being targeted and affected by MWU. The use of multiple transducers to deliver MWU to discrete brain regions simultaneously may enable the rapid and discretized characterization of the mechanobiological properties of distributed brain regions with appropriate scaled spatial resolutions with respect to the local generation of tissue strain.

Systems, devices, and methods of the present invention may comprise mechanically disturbing central nervous system tissues including the brain by providing ultrasound during MRI or NMR imaging sessions to conduct magnetic resonance elastography (MRE). MRE can be treated as a special case of flow encoding by defining the motion of the spins monitored by MRI, due to the external displacement, as a traveling wave.

The speeds at which longitudinal (compression) mechanical waves propagate in tissues can be described by $c_l=(K/\rho)^{1/2}$ where $c_l$ is the longitudinal wave speed and $\rho$ is the mass density of the tissue. The speed at which shear waves propagate in tissues can be described by $c_s=(G/\rho)^{1/2}$ where $c_s$ is the shear wave speed.

The displacement vector of a wave traveling in an isotropic homogenous elastic medium may be given by the wave equation and is shown here accounting for both longitudinal and transverse motion:

$$\rho\frac{\partial^2 \vec{u}}{\partial t^2} = (\lambda + 2\mu)\nabla(\nabla \cdot \vec{u}) - \mu\nabla^2 \vec{u}$$

where $\vec{u}$ is the displacement vector, $\lambda$ the bulk modulus, $\mu$ the shear modulus, and $\rho$ the density of the material. The general solution of this equation yields the 3D displacement vector in the medium:

$$u(\vec{r},t)=u_0 \cos(\vec{k}\cdot\vec{r}-\omega t+\theta)$$

where $\vec{r}$ is the position vector, $\omega$ the angular frequency in rad/sec, $\theta$ is a phase offset, $u_0$ is the displacement amplitude, and $\vec{k}$ is the wave vector. Thus, the displacement of the spins in a single direction $\vec{x}(t)$ can be expressed as:

$$\vec{x}(t)=x_0+u_0 \cos(\vec{k}\cdot\vec{r}-\omega t+\theta)$$

where $x_0$ is the initial displacement, $\omega$ is the frequency of the tissue displacement, and $\theta$ is the phase offset between the tissue displacement and the motion encoding gradients.

The utility of elastography derives from the fact that the pathological and/or physiological conditions of the tissue are reflected in its mechanical properties. Tissue deformation is one response to applied strain, and depending on the material properties, can be either elastic, viscous, or both. Hooke's law is used to relate the stress tensor and strain tensor when the deformation is small: $\sigma=C\epsilon$ where $\sigma$ is the stress tensor, $\epsilon$ is the strain tensor, and $C$ is the elastic modulus tensor. The two components of C considered for isotropic materials are the Lame constants $\lambda$ and $\mu$ where $\mu$ is the shear modulus, which relates shear stress and strain and $\lambda$ relates the transverse strain to the longitudinal stress.

Other parameters used to mechanically characterize materials as previously described include the bulk elastic modulus (K, material change in volume due to stress), Young's modulus (E, ratio of longitudinal deformation due to longitudinal stress), and Poisson's ratio ($\upsilon$, describes material compressibility). For isotropic and Hookean materials, these parameters are all related with only two independent constants:

$$\lambda = \frac{E\sigma}{(1-2\sigma)(1+\sigma)} \quad \mu = \frac{E}{2(1+\sigma)} \quad K = \frac{E}{3(1-2\sigma)}$$
$$E = \frac{9K\mu}{3K+\mu} \quad \upsilon = \frac{3K-2\mu}{2(3K+\mu)}$$

Soft tissues exhibit properties of both solids (retains shape) and fluids (incompressible) and are neither isotropic nor Hookean. Their mechanical properties however can be approximated using the above parameters. The shear modulus of tissues has a wide dynamic range, varying by over five orders of magnitude among, various tissues, providing a good contrast in elasticity imaging.

The Elastogram is a map of the shear modulus $\mu$ and is calculated from the signal phase acquired using MRE. Various techniques have been implemented for the reconstruction of the elasticity map from measured displacement data (may also be referred to as a wave image). These techniques include Algebraic Inversion of the Differential Equation (AIDE), Local Frequency Estimation (LFE), and subzone based reconstruction.

In some embodiments, mechanical waves through ultrasound are delivered to targeted brain regions to monitor functionalized changes in the viscoelastic properties of brain circuits. As an example of this particular embodiment, ultrasound is targeted to the primary motor cortex to locally displace or disturb this region of brain tissue. Using ultrasound to displace tissues and generate shear waves within the targeted brain circuit, the shear modulus and elastic modulus may be derived using magnetic resonance elastography through the generation of an elastogram. Following baseline measurements of the shear and elastic moduli, the motor cortex may be activated through volitional and rhythmic finger tapping or other fine voluntary movements. During the activation of motor cortex, the tissue of the primary motor cortex may be displaced with ultrasound again and another series of shear and elastic measurements are made using MRE methods to generate an elastogram. The changes between the baseline shear and elastic moduli and those measured during activation will yield a signature of how mechanical properties change across levels of neural activity for which there is currently no precedence. This approach is hereby defined as functional magnetic resonance elastography (fMRE). Due to the ability to target discrete brain regions and brain circuits using single-element focused transducers or phased arrays, it is anticipated fMRE can be conducted on nearly any brain region of interest by applying methods and systems as those described above.

Methods, systems, and devices described by the present invention do not necessarily need to be limited to tissues of the central nervous system or brain. In fact, many of the advantages described for the use of MWU and LPU in brain displacement (such as enhanced targeting) can be applied to other soft tissues of the body, for example muscle, liver, breast, and others.

In certain embodiments, systems and methods disclosed herein include using a transducer to emit (i.e., deliver, transmit, etc.) ultrasound residing in a time varying magnetic field to mechanically disturb (e.g., mechanically displace, induce mechanical motion, etc.) soft biological tissue (e.g., central nervous system tissue, brain tissue, etc.) to measure or otherwise acquire functionalized changes in the local shear, elastic, or bulk moduli of the soft biological tissue (e.g., in response to changes in neural activity). The systems and methods use these measurements to generate an elastogram of the soft biological tissue, such as for characterizing the mechanical properties of a normal, diseased, or traumatically injured brain.

In certain embodiments, systems and methods disclosed herein include conducting functional magnetic resonance elastography (fMRE) relying on tissue displacement (e.g., brain tissue displacement) achieved by emission of ultrasound from a transducer. In certain embodiments, the at least one transducer is single-element transducer, a plurality of single-element transducers, ten single-element transducers, or less than 100 single-element transducers, etc. In certain embodiments, a single-element transducer has a fixed focal length in a range of from about 20 to 200 millimeters.

In certain embodiments, multiple transducers are located at varied spatial positions positioned on the body or the head. In certain embodiments, increasing the number of ultrasound transducers increases the resolution of mechanical displacement in the target tissue. In certain embodiments, multiple transducers are used to concentrate strain resolution at a specific target within the tissue. In certain embodiments, systems and methods provide comparable tissue strains in multiple directions within the target tissue (as opposed to one principle direction using one transducer). In certain embodiments, multiple transducers are used to either serially or in parallel disturb targeted brain regions. In certain embodiments, the systems and methods include modulating and integrating strain information acquired through serial or parallel tissue displacements achieved using ultrasound. In certain embodiments, ultrasound transducers and their acoustic fields are localized for mechanically disrupting, compressing, or displacing central nervous system tissues, such as for directing localized peripheral ultrasonic neurostimulation. In certain embodiments, the systems and methods include tracking the position of an ultrasound transducer in relation to the head or body.

In certain embodiments, systems and methods include inducing mechanical motion in brain circuits using ultrasound composed of any single or multiple of acoustic frequencies ranging from about 0.1 to 2.0 MHz delivered from linear, annular, circular, or two-dimensional phased arrays. In certain embodiments, systems and methods include coupling an ultrasound transducer to the head to facilitate the transmission of ultrasound through the skin and skull into the brain to achieve local tissue displacement in the brain.

In certain embodiments, the ultrasound (e.g., focused ultrasound, planar ultrasound) comprises mesoscopic wavelength ultrasound (MWU) with an acoustic frequency from about 0.1 MHz to about 2 MHz and/or longitudinal wavelengths in brain tissues having a single or combination of spatial lengths ranging from about 0.3 to 16 millimeters (e.g., at variable acoustic frequencies). In certain embodiments, a single mesoscopic wavelength ultrasound waveform disturbs or otherwise imparts mechanical pressure on the brain, brain tissues, circuits, and/or nuclei for less than about 1, 10, 20, 25, 50, 100, 125, 250, 330, or 500 milliseconds when delivery is triggered. In certain embodiments, a single-element transducer transcranially transmits long-period ultrasound (LPU) having a single cycle time period ranging from about 0.5 to 10 microseconds in brain tissues. In certain embodiments, waveforms are constructed by one of more of convolution, addition, subtraction, multiplication, phase shifting, concatenation, stricking, modulation of amplitude, triggering, or any combination thereof.

In certain embodiments, the system and method includes a laser range finder; an ultrasonic range finder, an accelerometer, a gyroscope, a tilt sensor, a photodiode, a light-emitting diode, and/or an infrared emitting source and sensor, etc. In certain embodiments, systems and methods include hardware-timed synchronization or triggering. For example, in certain embodiments, systems and methods include TTL, CMOS, ECL, LVTTL, LVCMOS, LVPECL or other logic levels for the triggering and synchronization of ultrasound waveforms for mechanically disturbing central nervous system tissues during imaging methods (e.g., MRI, NMR, and/or ultrasound imaging). In certain embodiments, synchronization is achieved and ultrasound waveforms delivered at specific phases of respiration or cardiac cycles. In certain embodiments, systems and methods include software to gate triggering in the context of sham control, interleaving, randomization, and/or event-related or block-design. In certain embodiments, systems and methods include a delay block integrated circuit to allow control of consistent timing offsets between displacement and imaging modalities.

In certain embodiments, systems and methods enable an operator to modulate ultrasound parameters for disturbing, compressing, or displacing central nervous system tissues. In certain embodiments, the operator can change the ultrasound pulse duration, pulse repetition frequency, acoustic frequency, acoustic intensity, peak displacement pressure, ultrasound period, and/or longitudinal wavelength, etc.

In certain embodiments, systems and methods include monitoring changes in the mechanical properties of brain tissues (e.g., brain circuits) across time for an individual, where ultrasound is used to displace brain circuits or nuclei to generate an elastogram or derive the shear or elastic moduli of local brain circuits. In certain embodiments, the monitoring is in response to disease states, such as Alzheimer's disease, Parkinson's disease, essential tremor, epilepsy and other neurological disorders. In certain embodiments, the monitoring is in response to a head injury, concussion, or traumatic brain injury.

In certain embodiments, brain targets of interest are functionally localized using electroencephalography, functional magnetic resonance imaging, MRI, or transcranial cranial magnetic stimulation prior to displacement of that brain circuit in a targeted manner using ultrasound. In certain embodiments, the systems and methods include a mechanical translation system for positioning ultrasound transducers to target and locally displace tissues within an identified brain circuit. In certain embodiments, systems and methods include mechanical positioning of transducers, which is composed of MR-compatible materials, such as Teflon®, Delrin®, or other plastics or polymers or other MR-compatible materials (e.g., titanium or aluminum alloys).

In certain embodiments, systems and methods include computer devices executing software and/or algorithms for processing, post-processing, and/or inversion procedures to generate an elastogram from wave or MRI images acquired during the interleaved, asynchronous, or synchronous displacement of brain tissues using ultrasound.

Figure 14:
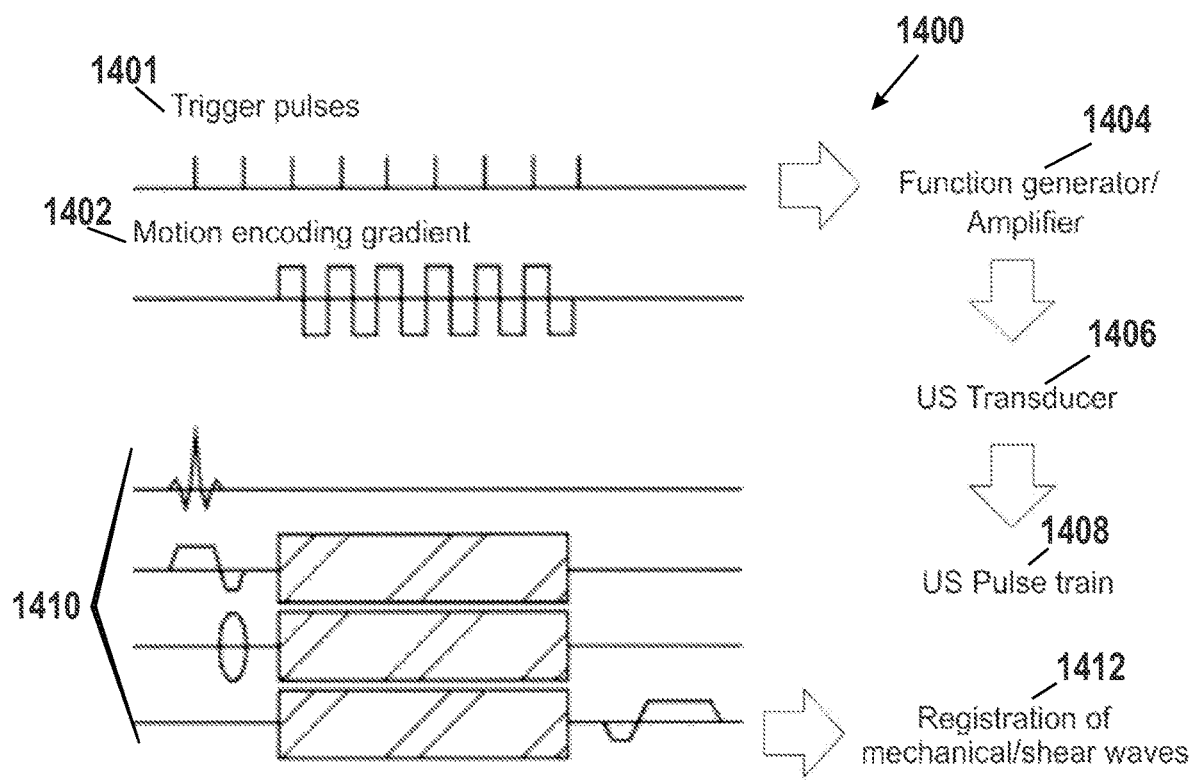
FIG. 14 is a flow chart illustrating synchronization of ultrasound-mediated brain tissue displacement during the acquisition of MRI data.
Figure 15:
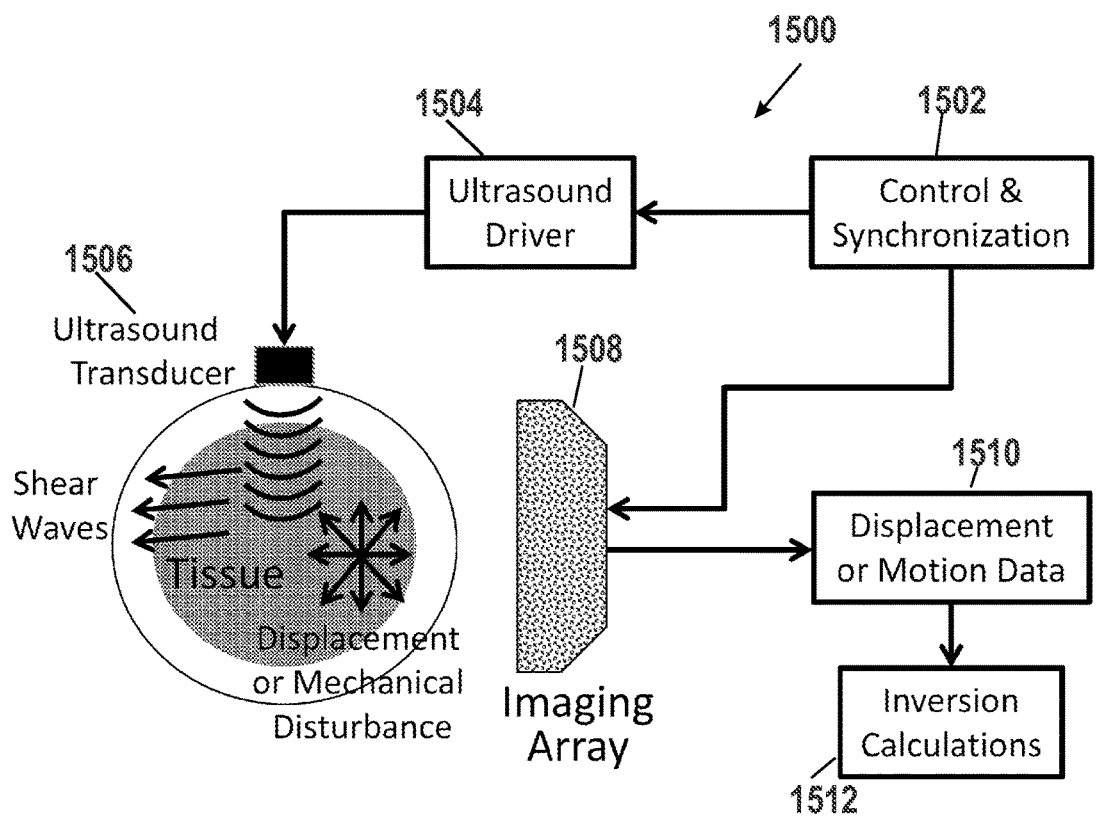
FIG. 15 is a flow chart illustrating collection of data to develop an elastogram from tissue disturbances introduced by ultrasound.

FIGS. 14 and 15 illustrate approaches to conducting elastographic imaging combined with brain disturbance using ultrasound. In particular, FIGS. 14 and 15 are flow charts illustrating the basic strategy for synchronizing ultrasound-mediated brain tissue displacement during the acquisition of MRI data.

FIG. 14 is a flowchart 1400 illustrating trigger pulses 1401 and motion encoding gradient 1402 are electronically transmitted to a function generator 1404, which then electronically transmits to a transducer 1406, which electronically transmits to a pulse train 1408. Meanwhile, mechanical/shear waves 1410 are registered 1412.

FIG. 15 is a flow chart 1500 illustrating in greater detail the basic approach to collecting data needed to develop an elastogram from tissue disturbances introduced by ultrasound. In particular, a control and synchronization engine 1502 electronically controls an ultrasound driver 1504 which controls an ultrasound transducer 1506. The control and synchronization engine 1502 also controls an imaging array 1508, which generates and transmits displacement or motion data 1510. The system then applies inversion calculations 1512 to the displacement or motion data 1510 to generate the elastogram.

Figure 16:
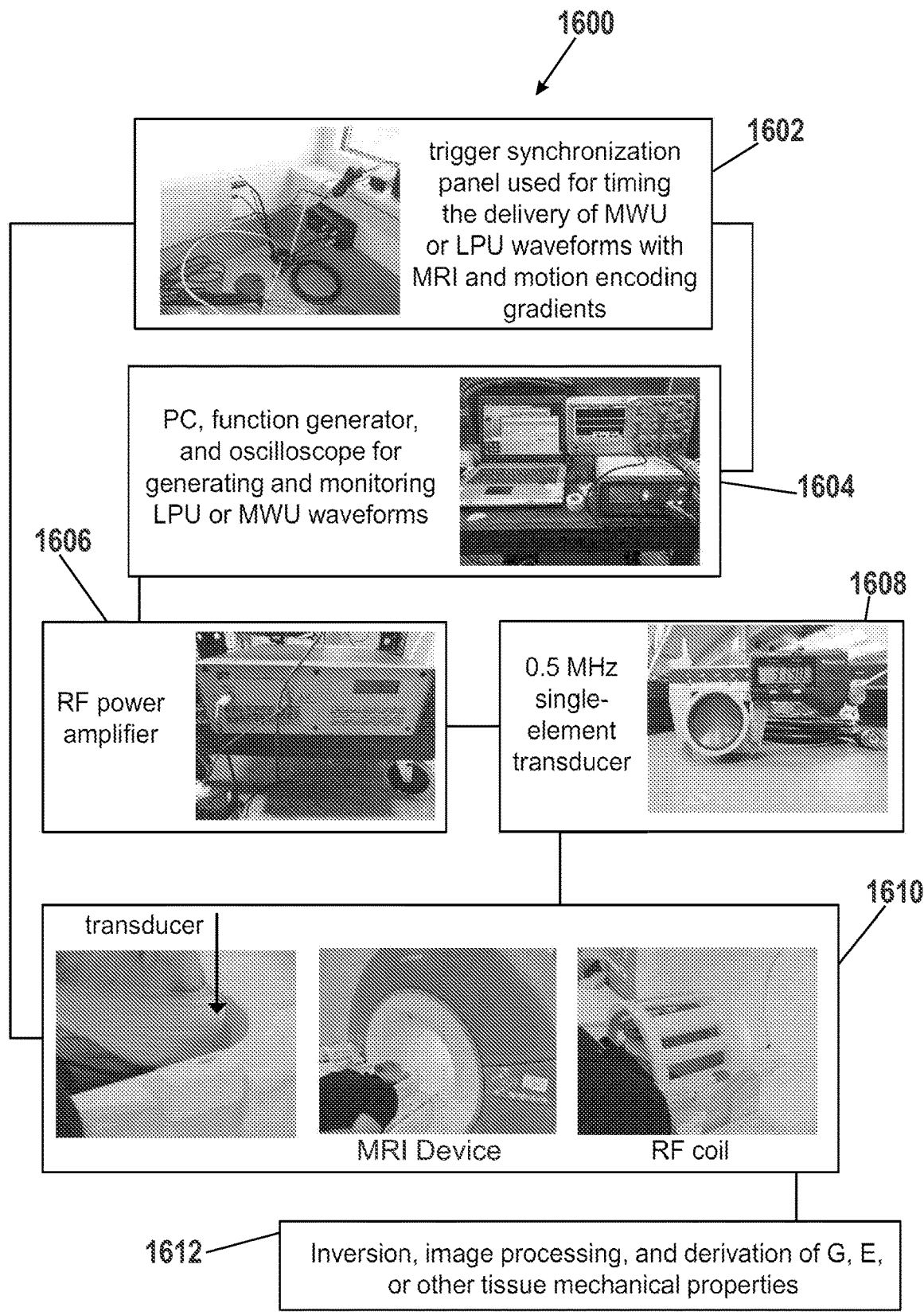
FIG. 16 is a flowchart identifying steps and selected elements of a system and method for mesomechanically disturbing brain circuits during MRI.

FIG. 16 is a flowchart 1600 illustrating steps and selected elements of a system and method for mesomechanically disturbing brain circuits during MRI. Step 1602 involves triggering of a synchronization panel used for timing the delivery of MWU or LPU waveforms with MRI and motion encoding gradients. In step 1604, a computer (e.g., PC), function generator, and oscilloscope are used for generating and monitoring LPU or MWU waveforms. In step 1606, waveforms generated in step 1604 are amplified with a RF power amplifier, and in step 1608, a 0.5 MHz single-element transducer converts the amplified waveforms to mechanical (vibratory) motion. In step 1610, the transducer is applied to the head of a subject, and the subject's head is placed in a MRI device having a proximate RF coil. In step 1612, inversion, image processing, and derivation of G, E, or other tissue mechanical properties are performed.

Figure 17A:
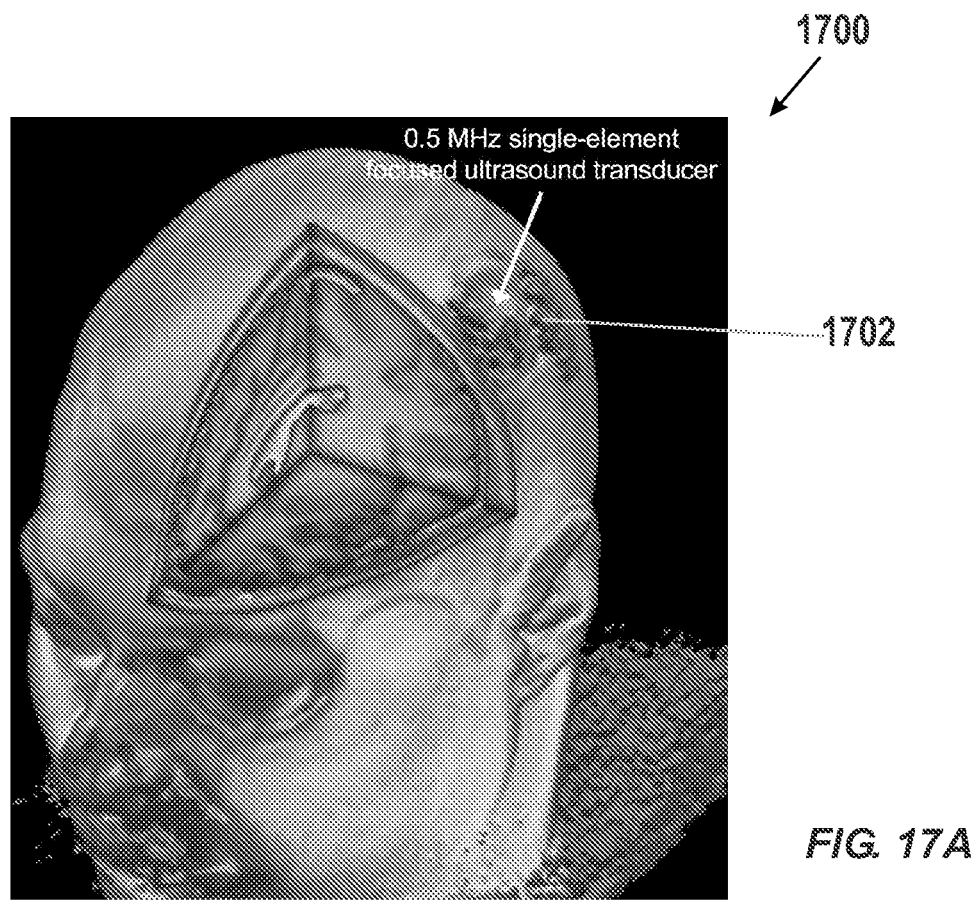
FIG. 17A is an MRI image acquired with ultrasound transducer targeting the primary motor cortex generated from a volume rendered series of MRI scans of the head of a human subject.
Figure 17B:
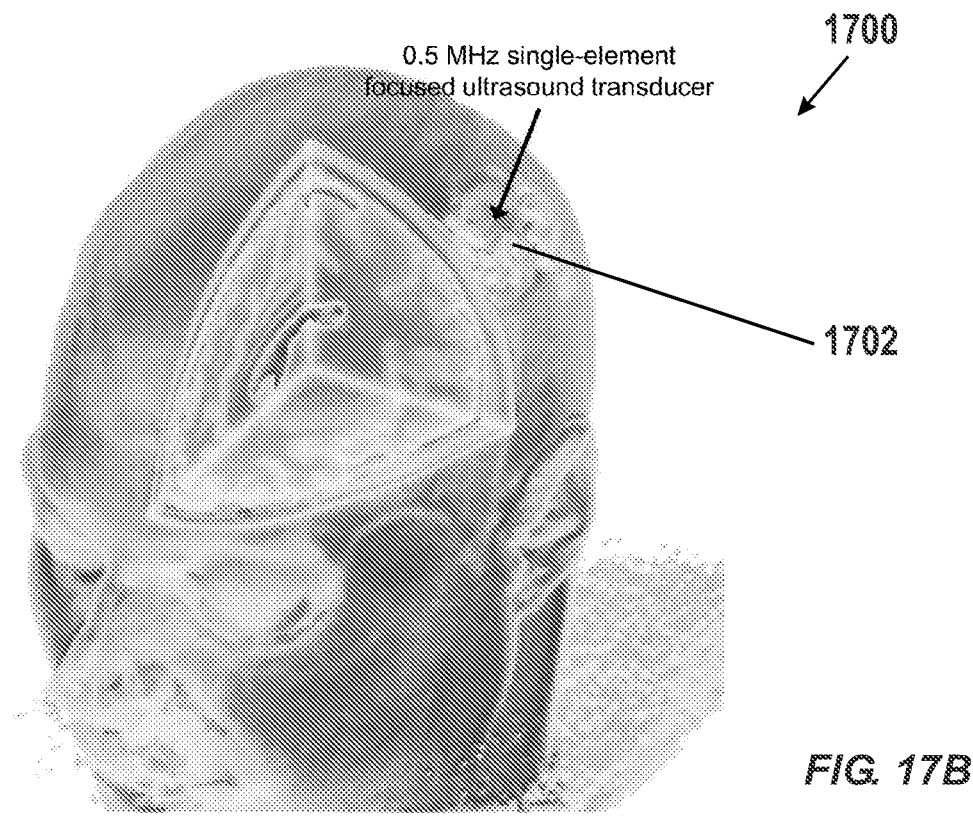
FIG. 17B is a color inverted version of the MRI image of FIG. 17B.

FIGS. 17A and 17B are MRI images 1700 acquired with an ultrasound transducer targeting the primary motor cortex. A volume-rendered series of MRI scans 1700 illustrates the placement of a 0.5 MHz single-element focused ultrasound transducer 1702 having a fixed focal length of about 35 mm. The positioning of the transducer 1702 may be made following functional location of the hand knob of the motor cortex using brain stimulation with transcranial magnetic stimulation.

Figure 18:
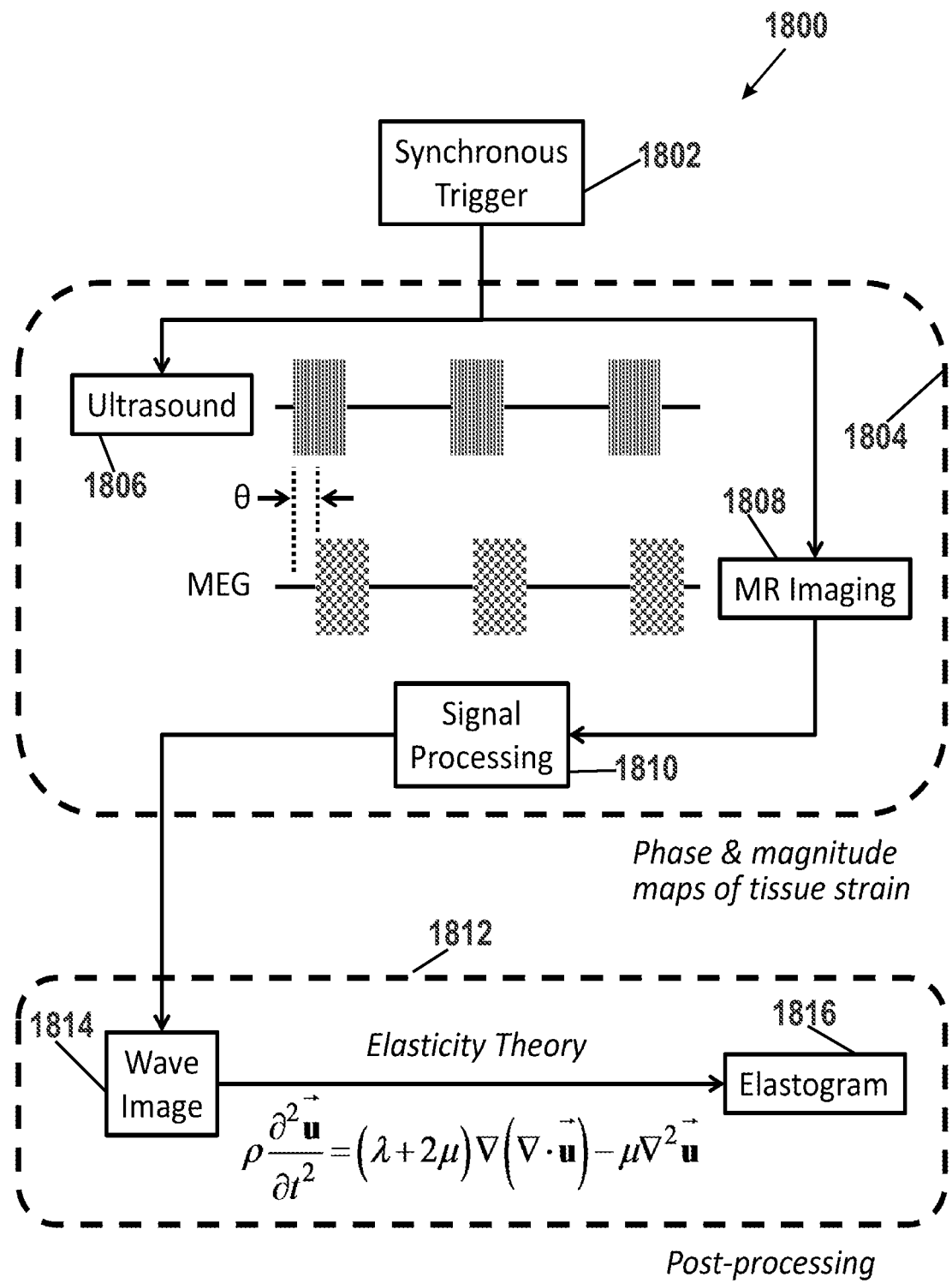
FIG. 18 is a flow chart illustrating image acquisition and MRI pulse sequence synchronization with motion encoding gradients to trigger the delivery of ultrasound for tissue displacement during magnetic resonance elastography procedures, as well as a general approach for generating elastograms from wave images through MRI scan processing and post-processing.

FIG. 18 is a flow chart 1800 illustrating the image acquisition and MRI pulse sequence synchronization with motion encoding gradients to trigger the delivery of ultrasound for tissue displacement during magnetic resonance elastography procedures. The flow chart 1800 also illustrates a general approach for generating elastograms from wave images through MRI scan processing and post-processing. In particular, in step 1802, a synchronous trigger is operated. In step 1804, phase and magnitude maps of tissue strain are generated. Within step 1804, ultrasound 1806 is emitted, MRI imaging 1808 is conducted, and signal processing 1810 is conducted. Step 1812 involves post-processing. Within post-processing 1812, a wave image 1814 is generated, and from that an elastogram 1816 is generated. FIG. 18 illustrates systems and methods for conducting magnetic resonance elastography or elastographic imaging combined with mesomechanical brain disturbance by transcranial ultrasound.

Figure 19:
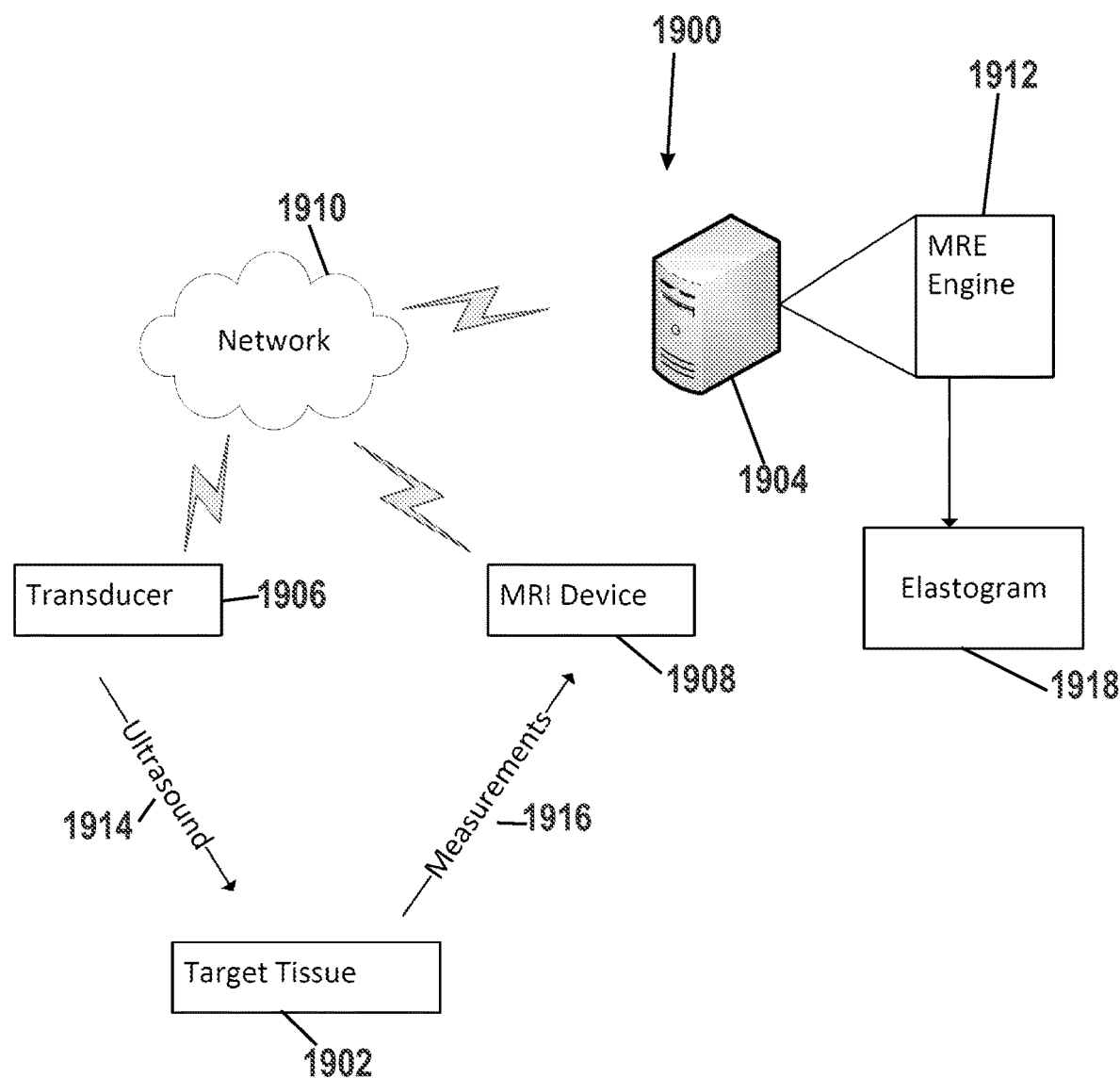
FIG. 19 is a schematic diagram illustrating a magnetic resonance elastography (MRE) system for generating an elastogram of at least a portion of a brain of a subject.

FIG. 19 is a schematic diagram of an MRE system according to one embodiment of the present disclosure. The MRE system 1900 generates an elastogram of at least a portion of a target tissue 1902 (e.g., brain of a subject). The MRE system 1900 includes a computing device 1904 in electronic communication with at least one transducer 1906 and with a magnetic resonance imaging (MRI) device 1908 (e.g., over a network 1910). The computing device 1904 includes at least one processor and a memory coupled to the at least one processor. An MRE engine 1912 electronically is stored in the memory of the computing device and executable by the at least one processor. The MRE engine 1912 is configured to electronically control operation of the at least one transducer 1906 to emit ultrasound 1914 at a frequency from 0.1 MHz to 1 MHz and with a longitudinal wavelength from 1.54 to 15.4 millimeters to locally displace target tissue 1902 (e.g., brain tissue of the subject). The MRE engine 1912 is further configured to electronically receive, from the MRI device 1908, at least one signal indicative of measurements 1916 of displacement of the target tissue 1902 (e.g., brain tissue) by the ultrasound 1914. The MRE engine 1912 is further configured to electronically generate an elastogram 1918 of the brain tissue based on the at least one signal.

Figure 20:
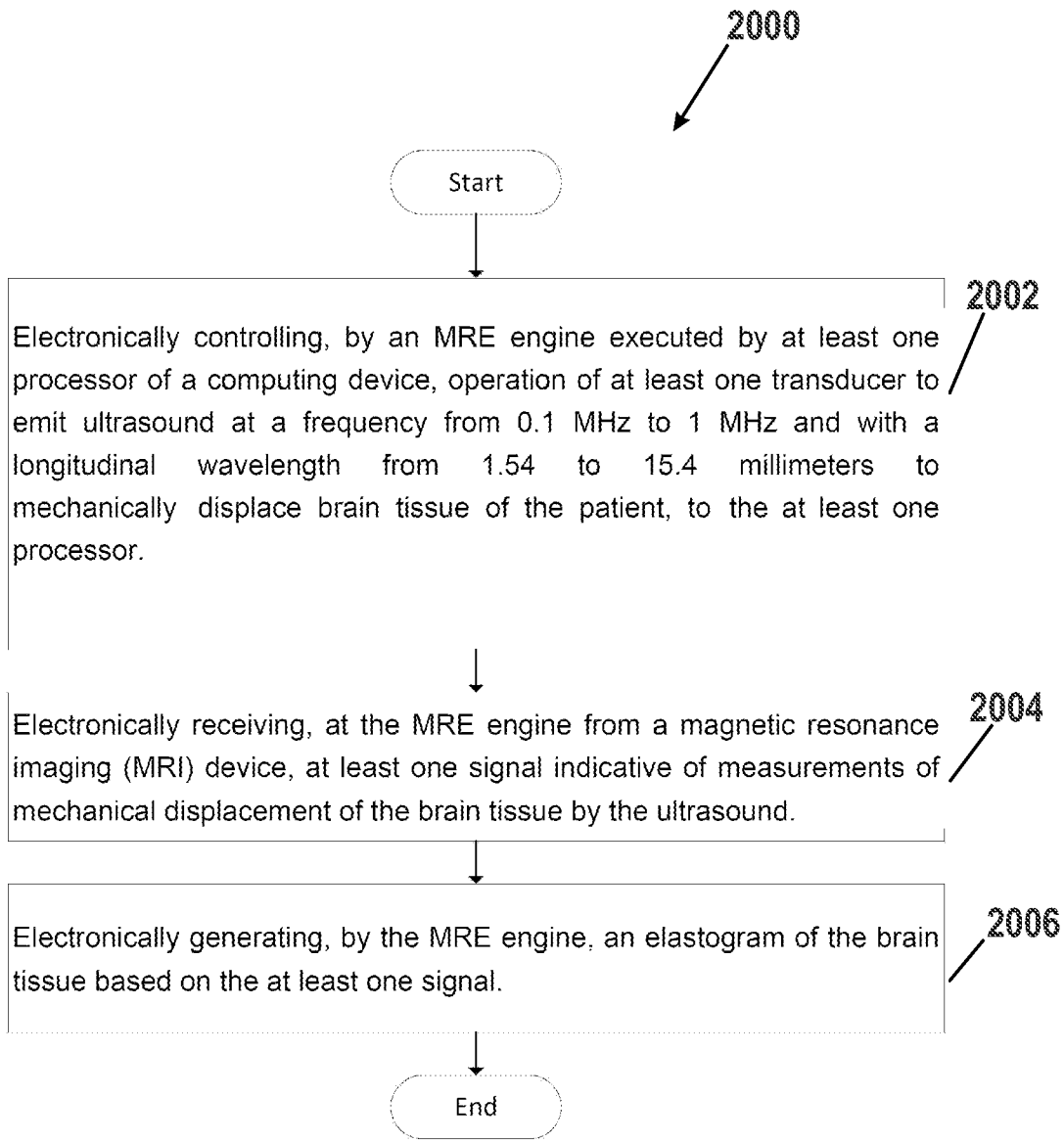
FIG. 20 is a flow chart illustrating steps for generating an elastogram of at least a portion of a brain of a subject.

FIG. 20 is a flowchart illustrating steps 2000 of a method for generating an elastogram of at least a portion of a brain of a subject that may be implemented using the system of FIG. 19. In particular, in step 2002, an MRE engine executed by at least one processor of a computing device electronically controls operation of at least one transducer to emit ultrasound at a frequency from 0.1 MHz to 1 MHz and with a longitudinal wavelength from 1.54 to 15.4 millimeters to mechanically displace brain tissue of the subject. The MRE engine is electronically stored in memory associated with the computing device and being coupled to the at least one processor. In step 2004, the MRE engine electronically receives from a magnetic resonance imaging (MRI) device at least one signal indicative of measurements of mechanical displacement of the brain tissue by the ultrasound. In step 2006, the MRE engine electronically generates an elastogram of the target tissue (e.g., brain tissue) based on the at least one signal.

Figure 21:
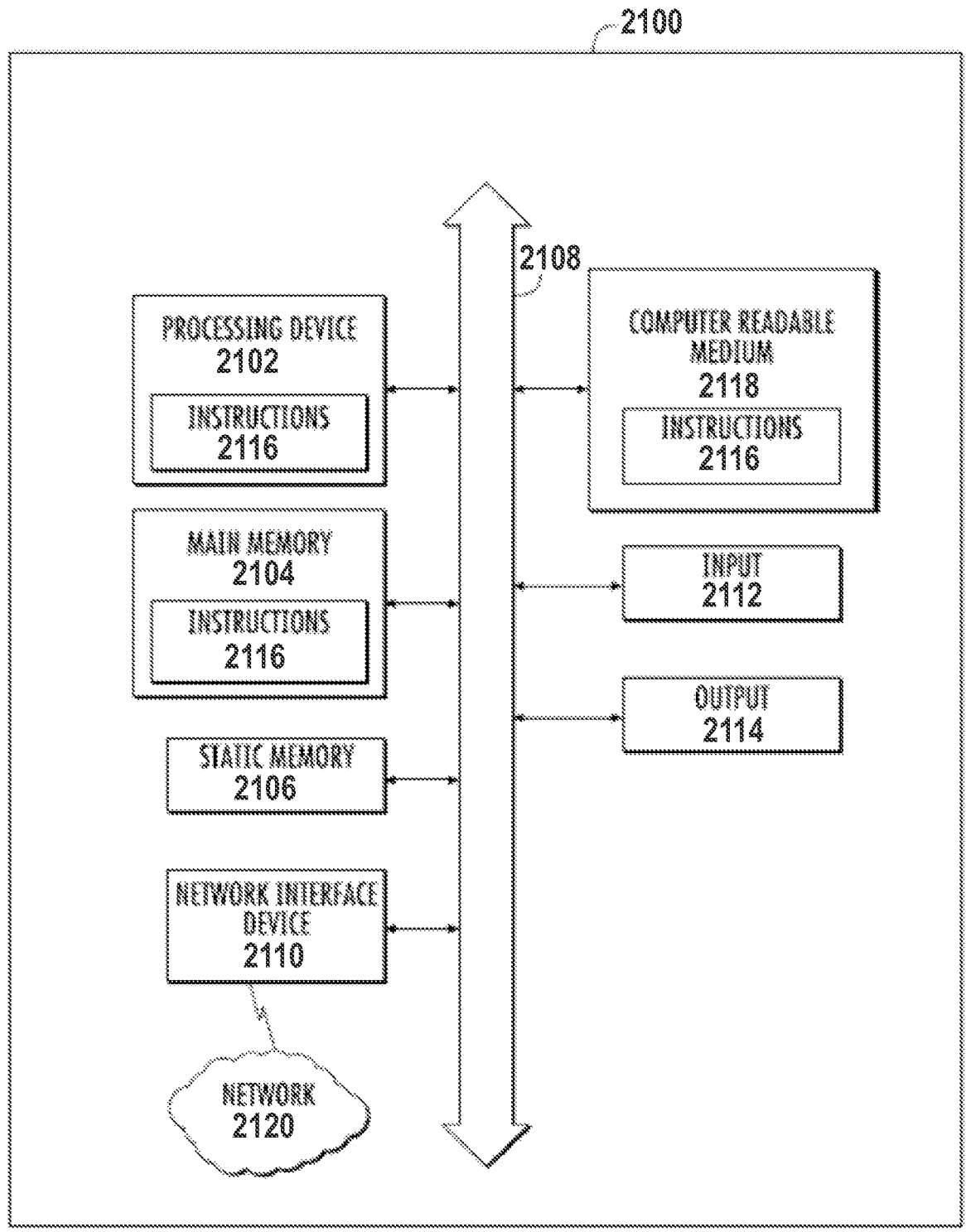
FIG. 21 is a schematic diagram of a generalized representation of a computer system that can be included in any component according to one embodiment.

FIG. 21 is a schematic diagram of a generalized representation of a computer system 2100 that can be included in any component of the systems or methods disclosed herein. In this regard, the computer system 2100 is adapted to execute instructions from a computer-readable medium to perform these and/or any of the functions or processing described herein.

In this regard, the computer system 2100 in FIG. 21 may include a set of instructions that may be executed to program and configure programmable digital signal processing circuits for supporting scaling of supported communications services. The computer system 2100 may be connected (e.g., networked) to other machines in a LAN, an intranet, an extranet, or the Internet. While only a single device is illustrated, the term "device" shall also be taken to include any collection of devices that individually or jointly execute a set (or multiple sets) of instructions to perform any one or more of the methodologies discussed herein. The computer system 2100 may be a circuit or circuits included in an electronic board card, such as a printed circuit board (PCB), a server, a personal computer, a desktop computer, a laptop computer, a personal digital assistant (PDA), a computing pad, a mobile device, or any other device, and may represent, for example, a server or a user's computer.

The computer system 2100 in this embodiment includes a processing device or processor 2102, a main memory 2104 (e.g., read-only memory (ROM), flash memory, dynamic random access memory (DRAM), such as synchronous DRAM (SDRAM), etc.), and a static memory 2106 (e.g., flash memory, static random access memory (SRAM), etc.), which may communicate with each other via a data bus 2108. Alternatively, the processing device 2102 may be connected to the main memory 2104 and/or static memory 2106 directly or via some other connectivity means. The processing device 2102 may be a controller, and the main memory 2104 or static memory 2106 may be any type of memory.

The processing device 2102 represents one or more general-purpose processing devices, such as a microprocessor, central processing unit, or the like. More particularly, the processing device 2102 may be a complex instruction set computing (CISC) microprocessor, a reduced instruction set computing (RISC) microprocessor, a very long instruction word (VLIW) microprocessor, a processor implementing other instruction sets, or other processors implementing a combination of instruction sets. The processing device 2102 is configured to execute processing logic in instructions for performing the operations and steps discussed herein.

The computer system 2100 may further include a network interface device 2110. The computer system 2100 also may or may not include an input 2112, configured to receive input and selections to be communicated to the computer system 2100 when executing instructions. The computer system 2100 also may or may not include an output 2114, including but not limited to a display, a video display unit (e.g., a liquid crystal display (LCD) or a cathode ray tube (CRT)), an alphanumeric input device (e.g., a keyboard), and/or a cursor control device (e.g., a mouse).

The computer system 2100 may or may not include a data storage device that includes instructions 2116 stored in a computer readable medium 2118. The instructions 2116 may also reside, completely or at least partially, within the main memory 2104 and/or within the processing device 2102 during execution thereof by the computer system 2100, the main memory 2104 and the processing device 2102 also constituting computer readable medium. The instructions 2116 may further be transmitted or received over a network 2120 via the network interface device 2110.

While the computer readable medium 2118 is shown in an embodiment to be a single medium, the term "computer-readable medium" should be taken to include a single medium or multiple media (e.g., a centralized or distributed database, and/or associated caches and servers) that store the one or more sets of instructions. The term "computer readable medium" shall also be taken to include any medium that is capable of storing, encoding, or carrying a set of instructions for execution by the processing device and that cause the processing device to perform any one or more of the methodologies of the embodiments disclosed herein. The term "computer readable medium" shall accordingly be taken to include, but not be limited to, solid-state memories, optical medium, and magnetic medium.

The embodiments disclosed herein include various steps. The steps of the embodiments disclosed herein may be formed by hardware components or may be embodied in machine-executable instructions, which may be used to cause a general-purpose or special-purpose processor programmed with the instructions to perform the steps. Alternatively, the steps may be performed by a combination of hardware and software.

The embodiments disclosed herein may be provided as a computer program product, or software, that may include a machine-readable medium (or computer readable medium) having stored thereon instructions which may be used to program a computer system (or other electronic devices) to perform a process according to the embodiments disclosed herein. A machine-readable medium includes any mechanism for storing or transmitting information in a form readable by a machine (e.g., a computer). For example, a machine-readable medium includes: a machine-readable storage medium (e.g., ROM, random access memory ("RAM"), a magnetic disk storage medium, an optical storage medium, flash memory devices, etc.); and the like.

Unless specifically stated otherwise and as apparent from the previous discussion, it is appreciated that throughout the description, discussions utilizing terms such as "processing," "computing," "determining," "displaying," or the like, refer to the action and processes of a computer system, or a similar electronic computing device, that manipulates and transforms data and memories represented as physical (electronic) quantities within the computer system's registers into other data similarly represented as physical quantities within the computer system memories or registers or other such information storage, transmission, or display devices.

The algorithms and displays presented herein are not inherently related to any particular computer or other apparatus. Various systems may be used with programs in accordance with the teachings herein, or it may prove convenient to construct more specialized apparatuses to perform the required method steps. The required structure for a variety of these systems is disclosed in the description above. In addition, the embodiments described herein are not described with reference to any particular programming language. It will be appreciated that a variety of programming languages may be used to implement the teachings of the embodiments as described herein.

Those of skill in the art will further appreciate that the various illustrative logical blocks, modules, circuits, and algorithms described in connection with the embodiments disclosed herein may be implemented as electronic hardware, instructions stored in memory or in another computer readable medium and executed by a processor or other processing device, or combinations of both. The components of the system described herein may be employed in any circuit, hardware component, integrated circuit (IC), or IC chip, as examples. Memory disclosed herein may be any type and size of memory and may be configured to store any type of information desired. To clearly illustrate this interchangeability, various illustrative components, blocks, modules, circuits, and steps have been described above generally in terms of their functionality. How such functionality is implemented depends on the particular application, design choices, and/or design constraints imposed on the overall system. Skilled artisans may implement the described functionality in varying ways for each particular application, but such implementation decisions should not be interpreted as causing a departure from the scope of the present embodiments.

The various illustrative logical blocks, modules, and circuits described in connection with the embodiments disclosed herein may be implemented or performed with a processor, a Digital Signal Processor (DSP), an Application Specific Integrated Circuit (ASIC), a Field Programmable Gate Array (FPGA), or other programmable logic device, a discrete gate or transistor logic, discrete hardware components, or any combination thereof designed to perform the functions described herein. Furthermore, a controller may be a processor. A processor may be a microprocessor, but in the alternative, the processor may be any conventional processor, controller, microcontroller, or state machine. A processor may also be implemented as a combination of computing devices (e.g., a combination of a DSP and a microprocessor, a plurality of microprocessors, one or more microprocessors in conjunction with a DSP core, or any other such configuration).

The embodiments disclosed herein may be embodied in hardware and in instructions that are stored in hardware, and may reside, for example, in RAM, flash memory, ROM, Electrically Programmable ROM (EPROM), Electrically Erasable Programmable ROM (EEPROM), registers, a hard disk, a removable disk, a CD-ROM, or any other form of computer readable medium known in the art. A storage medium is coupled to the processor such that the processor can read information from, and write information to, the storage medium. In the alternative, the storage medium may be integral to the processor. The processor and the storage medium may reside in an ASIC. The ASIC may reside in a remote station. In the alternative, the processor and the storage medium may reside as discrete components in a remote station, base station, or server.

It is also noted that the operational steps described in any of the embodiments herein are described to provide examples and discussion. The operations described may be performed in numerous different sequences other than the illustrated sequences. Furthermore, operations described in a single operational step may actually be performed in a number of different steps. Additionally, one or more operational steps discussed in the embodiments may be combined. Those of skill in the art will also understand that information and signals may be represented using any of a variety of technologies and techniques. For example, data, instructions, commands, information, signals, bits, symbols, and chips, which may be referenced throughout the above description, may be represented by voltages, currents, electromagnetic waves, magnetic fields, particles, optical fields, or any combination thereof.

Unless otherwise expressly stated, it is in no way intended that any method set forth herein be construed as requiring that its steps be performed in a specific order. Accordingly, where a method claim does not actually recite an order to be followed by its steps, or it is not otherwise specifically stated in the claims or descriptions that the steps are to be limited to a specific order, it is in no way intended that any particular order be inferred.

It is contemplated that any or more features or characteristics of any one or more embodiments disclosed herein may be combined with those of other embodiments, unless specifically indicated to the contrary herein.

Those skilled in the art will recognize improvements and modifications to the exemplary embodiments of the present disclosure. All such improvements and modifications are considered within the scope of the concepts disclosed herein and the claims that follow.

What is claimed is:

1. A magnetic resonance elastography (MRE) system for generating an elastogram of at least a portion of a brain of a subject, comprising:
    a plurality of ultrasonic transducers configured to concentrate localized strain resolution at a specific target from multiple directions, the specific target comprising a portion of brain tissue of the subject;
    a computing device in electronic communication with the plurality of transducers and with a magnetic resonance imaging (MRI) device, the computing device comprising at least one processor and a memory coupled to the at least one processor, wherein the at least one processor is configured to:
    electronically control operation of the plurality of ultrasound transducers to emit ultrasound at a frequency from 0.1 MHz to 1 MHz and with a longitudinal wavelength from 1.54 to 15.4 millimeters to locally displace brain tissue of the subject;
    electronically trigger synchronized displacement of the brain tissue by the plurality of transducers during acquisition of at least one signal from the MRI device;
    electronically receive, from the MRI device, the at least one signal indicative of measurements of displacement of the brain tissue by the plurality of ultrasound transducers; and
    electronically generate an elastogram of the brain tissue based on the at least one signal.

2. The MRE system of claim 1, wherein the ultrasound comprises focused ultrasound.

3. The MRE system of claim 1, wherein the ultrasound comprises planar ultrasound.

4. The MRE system of claim 1, wherein the ultrasound has a cycle time period from 0.5 to 10 milliseconds in the brain tissue.

5. The MRE system of claim 1, wherein the plurality of transducers is configured to emit the ultrasound for at least one burst having a duration of less than 500 milliseconds.

6. The MRE system of claim 1, wherein the at least one processor_is further configured to control operation of the plurality of transducers to coordinate emission of ultrasound with one or more biological cycles of the subject.

7. The MRE system of claim 1, wherein the at least one processor_is further configured to derive at least one of shear moduli, elastic moduli, or bulk moduli of a brain circuit of the brain tissue.

8. A method for generating an elastogram of at least a portion of a brain of a subject, comprising:
    electronically controlling, by at least one processor of a computing device, operation of a plurality of transducers to emit ultrasound at a frequency from 0.1 MHz to 1 MHz and with a longitudinal wavelength from 1.54 to 15.4 millimeters to mechanically displace brain tissue of the subject, wherein the plurality of ultrasonic transducers is configured to concentrate localized strain resolution at a specific target within the brain tissue from multiple directions, the specific target comprising a portion of the brain tissue;
    electronically triggering synchronized displacement of the brain tissue by the plurality of transducers during acquisition of at least one signal from a magnetic resonance imaging (MRI) device;
    electronically receiving, at the at least one processor from the MRI device, the at least one signal indicative of measurements of mechanical displacement of the brain tissue by the plurality of ultrasound transducers; and
    electronically generating, by the at least one processor, an elastogram of the brain tissue based on the at least one signal.

9. The method of claim 8, wherein the ultrasound comprises focused ultrasound.

10. The method of claim 8, wherein the ultrasound comprises planar ultrasound.

11. The method of claim 8, further comprising emitting, from the plurality of transducers, the ultrasound for at least one burst having a duration of less than 500 milliseconds.

12. The method of claim 8, wherein the ultrasound has a cycle time period from 0.5 to 10 milliseconds in brain tissue.

13. The method of claim 8, further comprising controlling, by the at least one processor, operation of the plurality of transducers to coordinate emission of ultrasound with one or more biological cycles of the subject.

14. The method of claim 8, further comprising deriving, by the at least one processor, at least one of shear moduli, elastic moduli, or bulk moduli of a brain circuit of the brain tissue.

15. A non-transitory computer readable medium comprising program instructions for generating an elastogram of at least a portion of a brain of a subject, wherein the program instructions are configured for:

electronically controlling, by at least one processor of a computing device, operation of a plurality of transducers to emit ultrasound at a frequency from 0.1 MHz to 1 MHz and with a longitudinal wavelength from 1.54 to 15.4 millimeters to mechanically displace brain tissue of a subject, wherein the plurality of ultrasonic transducers is configured to concentrate localized strain resolution at a specific target within the brain tissue from multiple directions, the specific target comprising a portion of the brain tissue;

electronically triggering synchronized displacement of the brain tissue by the plurality of transducers during acquisition of at least one signal from a magnetic resonance imaging (MRI) device;

electronically receiving, at the at least one processor from the MRI device, measurements of mechanical displacement of the brain tissue by the plurality of ultrasound transducers;

electronically generating, by the at least one processor, an elastogram of the brain tissue based on the measurements; and deriving, by the at least one processor, at least one of shear moduli, elastic moduli, or bulk moduli of a brain circuit of the brain tissue.

16. The non-transitory computer readable medium of claim 15, wherein the program instructions are further configured for emitting, from the plurality of ultrasound transducers, the ultrasound for at least one burst having a duration of less than 500 milliseconds.

17. The non-transitory computer readable medium of claim 15, wherein the program instructions are further configured for controlling, by the at least one processor, operation of the plurality of ultrasound transducers to coordinate emission of ultrasound with one or more biological cycles of the subject.

18. The non-transitory computer readable medium of claim 15, wherein the ultrasound has a cycle time period from 0.5 to 10 milliseconds in the brain tissue.

* * * * *